United States Patent
De Strooper et al.

(10) Patent No.: US 7,198,903 B2
(45) Date of Patent: Apr. 3, 2007

(54) BINDING DOMAINS BETWEEN PRESENILINS AND THEIR SUBSTRATES AS TARGETS FOR DRUG SCREENING

(75) Inventors: Bart De Strooper, Hoeilaart (BE); Wim Annaert, Kontich (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 103 days.

(21) Appl. No.: 10/662,651

(22) Filed: Sep. 15, 2003

(65) Prior Publication Data

US 2004/0115734 A1    Jun. 17, 2004

Related U.S. Application Data

(63) Continuation of application No. PCT/EP02/03033, filed on Mar. 15, 2002.

(30) Foreign Application Priority Data

Mar. 16, 2001  (EP)  .................................. 01201015

(51) Int. Cl.
*G01N 33/53* (2006.01)
(52) U.S. Cl. ........................ 435/7.1; 435/7.2; 435/7.21; 435/219; 435/221; 530/324; 530/326; 530/327
(58) Field of Classification Search ...................... None
See application file for complete search history.

(56) References Cited

U.S. PATENT DOCUMENTS 5,187,153 A  *  2/1993  Cordell et al. ................. 514/12
5,604,131 A  *  2/1997  Wadsworth et al. ..... 435/320.1

FOREIGN PATENT DOCUMENTS

| WO | WO 99/21886 A1 | 5/1999 |
|----|----------------|--------|
| WO | WO 02/00882 A2 | 1/2002 |
| WO | WO 02/074804 A2 | 9/2002 |

OTHER PUBLICATIONS

Mickle JE et al. Genotype-phenotype relationships in cystic fibrosis. Med Clin North Am. May 2000; 84(3):597-607.*
Voet et al. Biochemistry. 1990. John Wiley & Sons, Inc. 126-128 and 228-234.*
Yan et al., Two-amino acid molecular switch in an epithelial morphogen that regulates binding to two distinct receptors. Science 290: 523-527, 2000.*
Tischer et al. Beta-amyloid precursor protein. Location of transmembrane domain and specificity of gamma-secretase cleavage. J Biol Chem. Sep. 6, 1996;271(36):21914-9.*
Zhong et al. Increased amyloid production from aberrant beta-amyloid precursor proteins. J Biol Chem. Apr. 22, 1994;269(16):12179-84.*
Yu, Gang, et al., "Nicastrin modulates presenilin-mediated *notch/blp-1* signal transduction and βAPP processing," 407 NATURE 48-54 (Sep. 2000).
International Search Report for International Application No. PCT/EP02/03033, dated Aug. 18, 2003 (7 pages).

* cited by examiner

*Primary Examiner*—Elizabeth Kemmerer
*Assistant Examiner*—Gregory S Emch
(74) *Attorney, Agent, or Firm*—TraskBritt

(57) ABSTRACT

The present invention relates to the identification of the molecular binding domains between presenilins and its substrates such as amyloid precursor protein and telencephalin. These binding domains can be efficiently used in drug screening assays to screen for compounds capable of modulating the interaction between presenilins and type I transmembrane proteins. The invention further relates to compounds capable of modulating the interaction.

10 Claims, 6 Drawing Sheets

A.

B.

C.

BINDING DOMAINS BETWEEN PRESENILINS AND THEIR SUBSTRATES AS TARGETS FOR DRUG SCREENING

CROSS-REFERENCE TO RELATED APPLICATION

This application is a continuation of PCT International Patent Application No. PCT/EP02/03033, filed on Mar. 15, 2002, designating the United States of America, and published, in English, as PCT International Publication No. WO 02/074804 A2 on Sep. 26, 2002, the contents of which is incorporated by this reference.

TECHNICAL FIELD

The present invention relates to the identification of the molecular binding domains between presenilins and its substrates such as amyloid precursor protein (APP) and telencephalin. These binding domains can be efficiently used in drug screening assays to screen for compounds capable of modulating the interaction between presenilins and type I transmembrane proteins. The invention further relates to compounds capable of modulating the interaction.

BACKGROUND

Presenilin 1 and 2 (PS1 and PS2) are highly homologous proteins implicated in familial Alzheimer's disease (FAD) (Rogaev et al., 1995; Sherrington et al., 1995). All FAD-mutations in the presenilins (PSs) increase the secretion of the highly amyloidogenic Aβ42 peptide, a major constituent of the plaques in the brains of Alzheimer's Disease (AD) patients (Citron et al., 1997; Duff et al., 1996; Scheuner et al., 1996). Aβ42- and the more abundant Aβ40-peptide are generated from the larger amyloid precursor protein (APP) by the consecutive action of two enzymes, β- and γ-secretases (De Strooper and Annaert, 2000; Haass and Selkoe, 1993; Selkoe, 1998). Several lines of evidence imply the PSs in γ-secretase activity. (i) Aβ secretion in cell lines and neurons derived from PS1 −/− or PS1 −/− PS2 −/− embryos is strongly inhibited while the α- and β-cleaved APP C-terminal stubs, the immediate substrates for γ-secretase, accumulate in these cells (De Strooper et al., 1998; Herreman et al., 2000; Naruse et al., 1998; Zhang et al., 2000). (ii) PSs are part of a multiprotein complex that exhibits γ-secretase activity in detergent extracts (Li et al., 2000). (iii) Indirect evidence implies two conserved aspartic acid residues of the transmembrane domains 6 and 7 in the catalytic activity of the γ-secretase (Wolfe et al., 1999). This putative active site displays remote similarity with the catalytic site of the bacterial type-4 prepilin peptidases (Steiner et al., 2000). (iv) Potent γ-secretase inhibitors designed to act as transition state analogues bind PSs (Esler et al., 2000; Li et al, 2000).

PSs are also required for the regulated intramembrane proteolysis of the Notch proteins (De Strooper et al., 1999; Struhl and Greenwald, 1999), thereby acting as molecular switches between proteolysis and cell signaling (Annaert and De Strooper, 1999; Brown et al., 2000). While the absolute requirement of PS for γ-secretase processing is thus clearly established, several observations indicate that a "PS is γ-secretase" hypothesis is probably too simplistic. PSs are, for instance, integrated into a multiprotein complex (Capell et al., 1998; Verdile et al., 2000; Yu et al., 1998) and one of its components, nicastrin, is apparently involved in the regulation of its proteolytic activity (Yu et al., 2000). Other observations also indicate that the exact role of PS in γ-secretase activity needs further scrutiny. For instance, the mutation of Asp257, one of the two aspartates of the putative catalytic site of PS, as well as certain other missense mutations in PS, inhibit Notch but not APP cleavage (Capell et al., 2000; Kulic et al., 2000). This is difficult to conciliate with the idea that the two aspartates constitute the active site of a single protease. Another paradox that needs further work is the discrepancy between the subcellular distribution of PSs and the sites where γ-secretase cleavage of APP or Notch is supposed to occur ("the spatial paradox": Annaert and De Strooper, 1999; Annaert et al., 1999). The complexity of the issues involved is illustrated by studies that demonstrate the role of PS in the Wnt/β-catenin signaling pathway. Several authors found that PS can bind proteins of the armadillo family. PS1 indirectly modulates Wnt signaling by stabilizing β-catenin (De Strooper and Annaert, 2001; Kang et al., 1999; Nishimura et al., 1999; Soriano et al., 2001; Zhang et al., 1998). As β-catenin binding to PS1 is independent of γ-secretase function (Saura et al., 2000) it follows that PS1 contains several functional domains, and regulates at least more than one signaling pathway. The exact molecular domains involved in the interaction between presenilin and its substrates are not known. In the current invention we have identified that presenilin is binding in a complex two-part to type I transmembrane regions. These novel binding regions are important targets for drug development for the modulation of presenilin mediated intramembrane cleavage and can be used, for example, for drug development in the fight against Alzheimer's disease. It has been shown in the art that presenilins are endoproteolysed yielding saturable and stable complexes of N-terminal and C-terminal fragments (NTF and CTF) (Thinakaran et al., 1996; Thinakaran et al., 1997) and that the integrity of PS including intramolecular interactions between both fragments, is required for its normal biological function (Saura et al., 1999; Tomita et al., 1998). It has also been shown that co-immunoprecipitation of Notch with the PS1-NTF as well as with the PS1-CTF can occur (Ray et al., 1999), although the exact binding sites were not identified. Furthermore mutational analysis has demonstrated that the C-terminus of PS is needed for the stabilization, endoproteolysis and Aβ42 overproduction caused by FAD-linked mutations (Thinakaran et al., 1997; Tomita et al., 1999).

DISCLOSURE OF THE INVENTION

In the present invention we have identified a novel substrate for presenilin. More specifically, a specific interaction of the type I transmembrane protein telencephalin (TLN) with PS1 and PS2 is found. TLN is a neuron and region specific member of the ICAM subfamily of intercellular adhesion molecules (Hayflick et al., 1998; Yoshihara and Mori, 1994). It has been shown that TLN promotes dendritic outgrowth (Tamada et al., 1998; Tian et al., 2000) and contributes to long-term potentiation (Nakamura et al., 2001; Sakurai et al., 1998). The analogy with Notch in promoting dendritic branching (Berezovska et al., 1999; Sestan et al., 1999), and the downregulation of TLN in the brains of AD-patients (Hino et al., 1997), motivated us to investigate the PS1-TLN interaction in detail. We have delineated precisely the binding sites in PS1 and TLN, and can extend those investigations towards APP. Our findings can be integrated into a novel binding model for presenilins with type I transmembrane proteins. Two domains at opposing sites in the PS1 sequence are involved in TLN and also in APP binding. Our results therefore indicate that type I integral membrane proteins can bind via their transmembrane domain to a common binding pocket constituted by the carboxyterminal domain and the first integral membrane domain of PS1. We could not demonstrate any binding in vitro between APP, nor TLN (or fragments derived thereof) with the hydrophilic N-terminus of PS1. The fact that the binding domains we identified in PS1 are exceptionally well conserved among different species further corroborates our hypothesis that they are of major functional importance. Consistently, only few disease-linked mutations are found in these regions (Cruts and Van Broeckhoven, 1998; see also AD Mutation Database) while some loss-of-function mutations in these domains in the PS homologues of *C. elegans* (Arduengo et al., 1998; Levitan and Greenwald, 1995; Okochi et al., 2000) and *Drosophila* (Lukinova et al., 1999) have been reported. If both domains, as we demonstrate here, comprise together a functional pocket binding the transmembrane regions of TLN and APP, they should be spatially closely juxtaposed to each other. This indicates for a circular or ring-like structure for PS1. Such a model supports recent findings that intramolecular associations between different domains of PS1 as well as cooperative interactions between both fragments are important for the functionality of the PS complex (Saura et al., 1999; Tomita et al., 1998).

The invention provides in one embodiment an isolated complex between presenilin and a type I transmembrane protein characterized by binding domains comprising a) the first transmembrane domain of presenilin, b) the last eight carboxyterminal amino acids of presenilin and c) the transmembrane domain of said type I transmembrane protein. A presenilin can be either presenilin 1 or presenilin 2. With the term "complex" here it is meant an interaction between at least two domains of one or more proteins. The interaction between proteins is known in the art and includes electrostatic and hydrophobic interactions. Type I transmembrane proteins are also known in the art and the type I transmembrane proteins include substrates of presenilins such as amyloid precursor protein (APP), Notch, cadherins such as E-cadherin, Nicastrin, alfa-secretase, beta-secretase, members of the ICAM-protein family such as telencephalin (TLN).

In another embodiment, the invention provides a binding domain of an isolated complex between presenilin and a type I transmembrane protein consisting essentially of the first transmembrane domain of presenilin, set forth by SEQ ID NO:1 or SEQ ID NO:2 in the accompanying Sequence Listing that is incorporated by this reference, and fragments and variants thereof. The variants include modifications of the amino acid sequence set forth in SEQ ID NO:1 or SEQ ID NO:2 and longer sequences that include SEQ ID NO:1 or SEQ ID NO:2. Fragments of SEQ ID NO:1 or SEQ ID NO:2 are sequences that are derived thereof. Fragments and variants belong to the present invention as long as they have the capability of binding in the complex.

In yet another embodiment, the invention provides a binding domain of an isolated complex between presenilin and a type I transmembrane protein consisting essentially of the last eight carboxyterminal amino acids of presenilin, set forth by SEQ ID NO:3 or SEQ ID NO:4 and fragments and variants thereof.

In yet another embodiment, the invention provides a binding domain of an isolated complex between presenilin and a type I transmembrane protein consisting essentially of a sequence of APP set forth by SEQ ID NO:5 and fragments and variants thereof.

In yet another embodiment, the invention provides a binding domain of an isolated complex between presenilin and a type I transmembrane protein consisting essentially of a sequence of TLN set forth by SEQ ID NO:6 and fragments and variants thereof.

In a further embodiment, the isolated complex between presenilin and a type I transmembrane protein or the separate binding domains between presenilin and a type I transmembrane can be used to identify compounds that modify the interaction between presenilin and type I transmembrane protein. The method includes treating the complex or the separate binding domains with at least one compound, and monitoring of interaction between the presenilin protein and a type I transmembrane protein.

"Compound" as used herein means any anorganic or organic compound, including simple or complex inorganic or organic molecules, peptides, peptido-mimetics, proteins, antibodies, carbohydrates, nucleic acids or derivatives thereof.

A compound can modulate the interaction and, consequently, this means that a compound can have an antagonizing effect (be an antagonist or an activator) on the interaction and disrupt or prevent the interaction, or may have an agonizing effect (be an agonist or an inhibitor) on the interaction and can make the interaction stronger. Monitoring includes measuring of the effect of the compound on the interaction between presenilin and a type I transmembrane protein. The monitoring may be done biochemically by purifying the binding domains and measuring the interaction between the binding domains upon treatment with at least one compound. Alternatively, monitoring may be measured in an assay comprising cellular and cell-free assays. A non-limiting example of such an assay may be the measurement of presenilin mediated transmembrane cleavage such as for example gamma-secretase cleavage of APP. This type of proteolytic processing has been recently called "regulated intramembrane proteolysis" (rip) (Brown et al. (2000) Cell 100, 391). Presenilin 1 is also involved in the proteolytic processing of the transmembrane domain of other proteins like Notch, a signaling protein involved in cell fate decisions (De Strooper et al., 1999, Nature 398, 518), and Ire1p, a protein involved in the control of the unfolded protein response (Niwa et al., 1999, Cell 99, 691) and based on this knowledge assays may be developed to monitor the effect of a compound on the interaction between presenilin and Notch or Irep.

In yet another embodiment, the invention provides a compound identified by the use of the herein before described method.

In still another embodiment, the invention provides a compound comprising SEQ ID NO:1 and SEQ ID NO:2 and fragments, variants, peptidomimetics thereof which bind to a type I transmembrane protein. Fragments and variants of SEQ ID NO:1 are part of this invention as long as they bind to a type I transmembrane protein that is a substrate for presenilin. Fragments of SEQ ID NO:1 are smaller than the amino acid set forth by SEQ ID NO:1. Variants include variations in the amino acid composition set forth by SEQ ID NO:1 and variants can also be longer sequences including the amino acid sequence of SEQ ID NO:1.

In yet another embodiment, the invention provides a compound comprising SEQ ID NO:3 and SEQ ID NO:4 and fragments, variants, peptidomimetics thereof which bind to a type I transmembrane protein.

In yet another embodiment, the invention provides a compound comprising SEQ ID NO:5 and fragments, variants, peptidomimetics thereof which bind to a presenilin.

In yet another embodiment, the invention provides a compound comprising SEQ ID NO:6 and fragments, variants, peptidomimetics thereof that bind to a presenilin.

In yet another embodiment, the invention provides a compound comprising SEQ ID NO:7 and fragments, variants, peptidomimetics thereof that bind to a presenilin.

In yet another embodiment, the invention provides a compound comprising SEQ ID NO:12 and fragments, variants, peptidomimetics thereof that bind to a presenilin.

In yet another embodiment, the invention provides a compound comprising SEQ ID NO:10 and fragments, variants, peptidomimetics thereof that bind to a type I transmembrane protein and more particularly to APP.

The term "peptido mimetic" means a molecule able to mimic the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems, which are similar to the biological activity of the peptide.

The peptidomimetic of this invention are preferably substantially similar in both three-dimensional shape and biological activity to the peptides set forth above. Substantial similarity means that the geometric relationship of groups in the peptide that react with for example a type I transmembrane protein is preserved. There are clear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are much cheaper to produce than peptides. Finally, there are problems associated with stability, storage and immunoreactivity for peptides that are not experienced with peptide mimetics. The peptides described in the present invention have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications may also be made by replacing chemical groups of the amino acids with other chemical groups of similar structure. The development of peptidomimetics may be aided by determining the tertiary structure of the original peptide, either free or bound to a substrate, e.g., presenilin or a transmembrane part of a type I transmembrane protein, by NMR spectroscopy, crystallography and/or computer-aided molecular modelling. These techniques aid in the development of novel compositions of higher potency and/or greater bioavailability and/or greater stability than the original peptide (Dean (1994), *BioEssays*, 16: 683–687; Cohen and Shatzmiller (1993), *J. Mol. Graph.*, 11: 166–173; Wiley and Rich (1993), *Med. Res. Rev.*, 13: 327–384; Moore (1994), *Trends Pharmacol. Sci.*, 15: 124–129; Hruby (1993), *Biopolymers*, 33: 1073–1082; Bugg et al. (1993), *Sci. Am.*, 269: 92–98, all incorporated herein by reference). Once a potential peptidomimetic compound is identified, it may be synthesized and assayed using the method described herein to assess its activity. Thus, through use of the methods described above, the present invention provides compounds exhibiting enhanced therapeutic activity in comparison to the peptides described above. The peptidomimetic compounds obtained by the above methods, having the biological activity of the above named peptides and similar three-dimensional structure, are encompassed by this invention. It will be readily apparent to one skilled in the art that a peptidomimetic may be generated from any of the modified peptides described in the previous section or from a peptide bearing more than one of the modifications described from the previous section. It will furthermore be apparent that the peptidomimetics of this invention can be further used for the development of even more potent non-peptidic compounds, in addition to their utility as therapeutic compounds.

In a further embodiment, the invention provides a method for the production of a pharmaceutical composition comprising using at least one compound identified via the complex, or binding domains thereof, of the present invention and mixing the compound or a derivative or homologue thereof with a pharmaceutically acceptable carrier.

The administration of a gene or compound or a pharmaceutically acceptable salt thereof may be by way of oral, inhaled or parenteral administration. The active compound may be administered alone or preferably formulated as a pharmaceutical composition. A unit dose will normally contain 0.01 to 50 mg for example 0.01 to 10 mg, or 0.05 to 2 mg of compound or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.05 to 10 mg. It is greatly preferred that the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case, the particles of active compound suitably have diameters of less than 50 microns, preferably less than 10 microns, for example between 1 and 5 microns, such as between 2 and 5 microns. A favored inhaled dose will be in the range of 0.05 to 2 mg, for example 0.05 to 0.5 mg, 0.1 to 1 mg or 0.5 to 2 mg. For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

In a further embodiment, one or more compounds identified in the invention can be used to modulate presenilin mediated processing of type I transmembrane proteins. As an unlimited example of presenilin mediated processing of type I transmembrane proteins is the presenilin-mediated cleavage of amyloid precursor protein, which leads to beta-amyloid production. Therefore the compounds or a combination thereof of the present invention can be used to inhibit the formation of beta-amyloid and are valuable to prevent or treat Alzheimer's disease.

In another embodiment, one or more compounds identified in the present invention may be used to modulate turnover of type I transmembrane proteins. Indeed, the data of the present invention, together with previous investigations, put presenilins at the crossroads of several important signaling pathways involving TLN, Notch, APP, Cadherin and β-catenin/Wnt. However, this invention not only shows a function of presenilins at the level of regulated intramembrane proteolysis but also points towards an additional role of presenilins on the control of the overall turnover of type I transmembrane proteins that interact with presenilins. In the present invention it is shown that the presenilin controls the turnover of telencephalin. It has been shown that TLN promotes dendritic outgrowth (Tamada et al., 1998; Tian et al., 2000) and contributes to long-term potentiation (Nakamura et al., 2001; Sakurai et al., 1998). Also a downregulation of TLN has been observed in the brains of AD-patients (Hino et al., 1997). Therefore, the present invention provides a way to modulate the turn-over of type I transmembrane proteins such as telencephalin, being a substrate for presenilin. The possibility to interfere is important for the treatment of Alzheimer's disease and/or to modulate memory formation.

Part A. Schematic drawing of the domain structure of telencephalin (TLN) including the nine Ig-like domains (I to IX). The protein fragment identified by 2-hybrid screening is displayed (TLN/256C). The epitope recognized by antibody B36.1 is indicated. "SS" indicates a disulfide bridge.

Part B. Both PS1 and PS2 bind endogenous TLN. Equal amounts of GST-PS1/39C and GST-PS2/39C fusion proteins, or GST alone were incubated with low salt brain extracts. Bound material was separated in 12% SDS-PAGE, blotted and probed with anti-TLN pab B36.1 (1/10,000).

Part C. The interaction of TLN with PS1/39C is salt-dependent. Triton X100 brain extracts were incubated with equal amounts of immobilized GST-PS1/39C in the presence of increasing salt concentrations. The bound material was analyzed as in FIG. 1, Part B.

Part D. The PS1-TLN interaction is specific. GST-PS1/39C or GST alone was incubated with (+) or without (−) brain extracts at low (75 mM) or high (400 mM) salt concentration. The bound material ("beads") was analyzed as above by western blotting using the antibodies indicated. Endogenous TLN was specifically retained on the immobilized GST-PS1/39C especially at 75 mM NaCl. Under those conditions, binding was quantitative as deduced from the absence of TLN signals in the unbound supernatant (sup, lane indicated with 75 mM, ⅓ of the input material). Other proteins such as synaptophysin, syntaxin or synaptobrevin II, or ER-specific proteins such as calnexin and PDI, did not interact. At long exposure times, a weak signal for endogenous APP could be demonstrated in the bound fractions.

Part E. Interaction of GST-TLN/256C with endogenous PS1. Immobilized GST-TLN/256C (see FIG. 1, Part A) was incubated with 1% Triton-X100 or 2% CHAPS extracts of mouse brain in the presence of the indicated salt concentrations. GST alone was used as a negative control. PS1-CTF was predominantly detected in the bound fraction of low salt 1% Triton-X100 brain extracts. When extracted with 2% CHAPS, both the PS1-NTF and PS1-CTF were bound to GST-TLN/256C. The difference between the intensity of the bands is due to different affinities of the pabs as shown for the crude extract ("Total" in first lane). Binding was largely abolished at high salt concentrations (400 mM). No binding was observed in the absence of extract or with GST-beads. Endogenous APP was found to bind as well and the relative amount of bound APP increased in 2% CHAPS brain extracts. No binding was observed with other proteins such as BAP31, synaptobrevin 11 and ductin.

Figure 2:
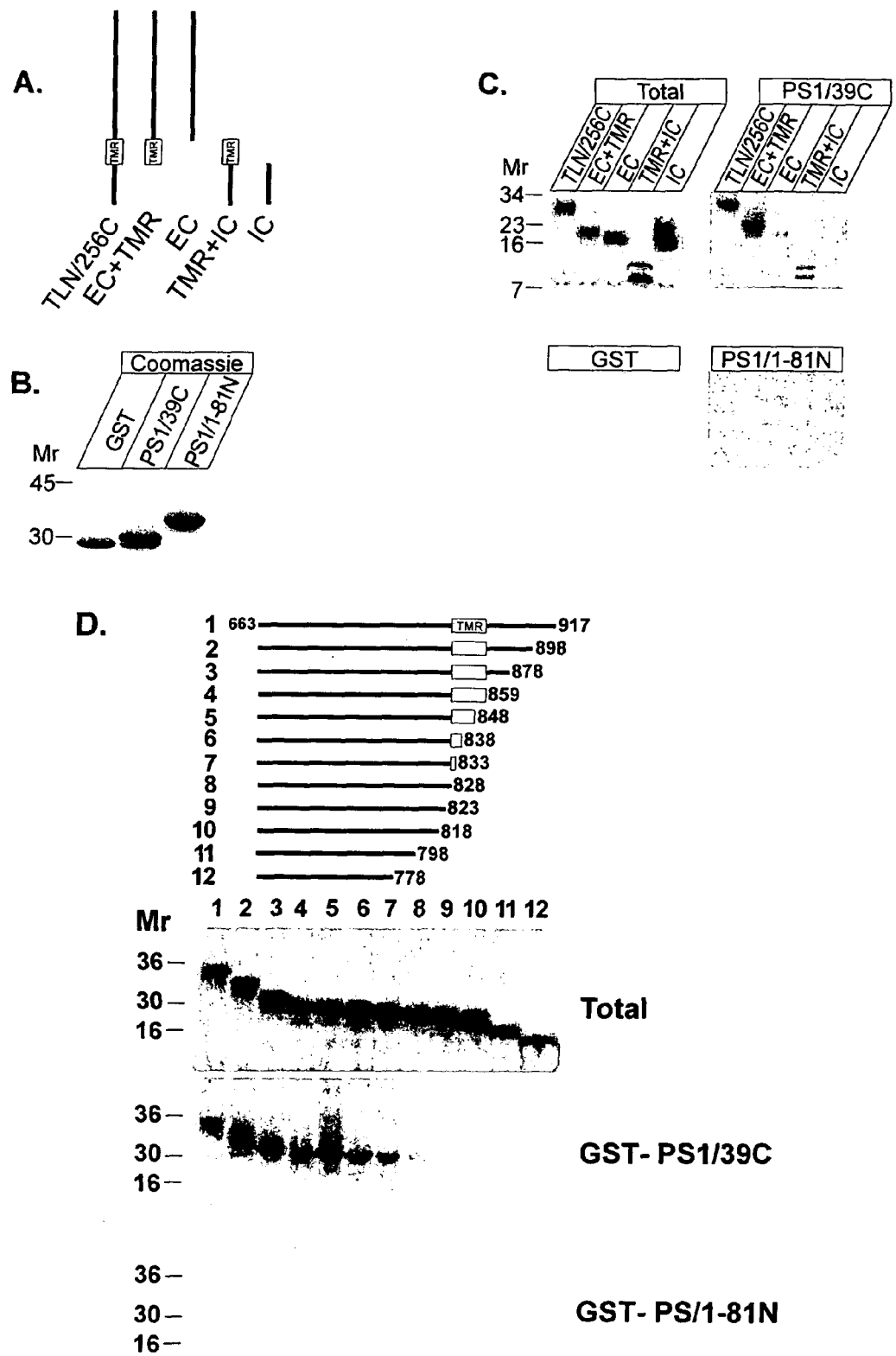

FIG. 2: PS1/39C binds to the transmembrane domain of TLN.

Part A. N- or C-terminal truncated mutants of TLN/256C were generated by in vitro transcription/translation and assayed for binding to GST, GST-PS1/39C or GST-PS1/1-81N (PS1 N-terminus fused to GST).

Part B. Coomassie staining of the different fusion proteins used in the binding reaction. Similar amounts of immobilized fusion proteins were used.

Part C. Total: autoradiogram of the translated, [$^{35}$S]-methionine labeled TLN constructs used for the binding reaction. Similar amounts of input material are used. Note the tendency of the intracellular domain (IC) to oligomerize. Only TLN/256C, and the TLN mutants that encompass the transmembrane domain (TMR) of TLN bind efficiently to immobilized GST-PS/39C. No binding was observed with GST alone or GST-PS1/1-81N (lower panels in FIG. 2, Part C). EC: ectodomain of TLN/256C.

Part D. Mapping of the binding domain of TLN. The top panel shows the different C-terminal truncated TLN mutants generated by in vitro transcription/translation. Radiolabeled translated products (Total) were assayed for binding to GST-PS1/39C (third panel), GST-PS1/1-81N (fourth panel) or GST alone (not shown). Binding becomes virtually abolished when the N-terminal 5 amino acids (Val$^{829}$-Trp$^{833}$) of the transmembrane region of TLN are deleted (construct 8 in top panel).

Figure 3:
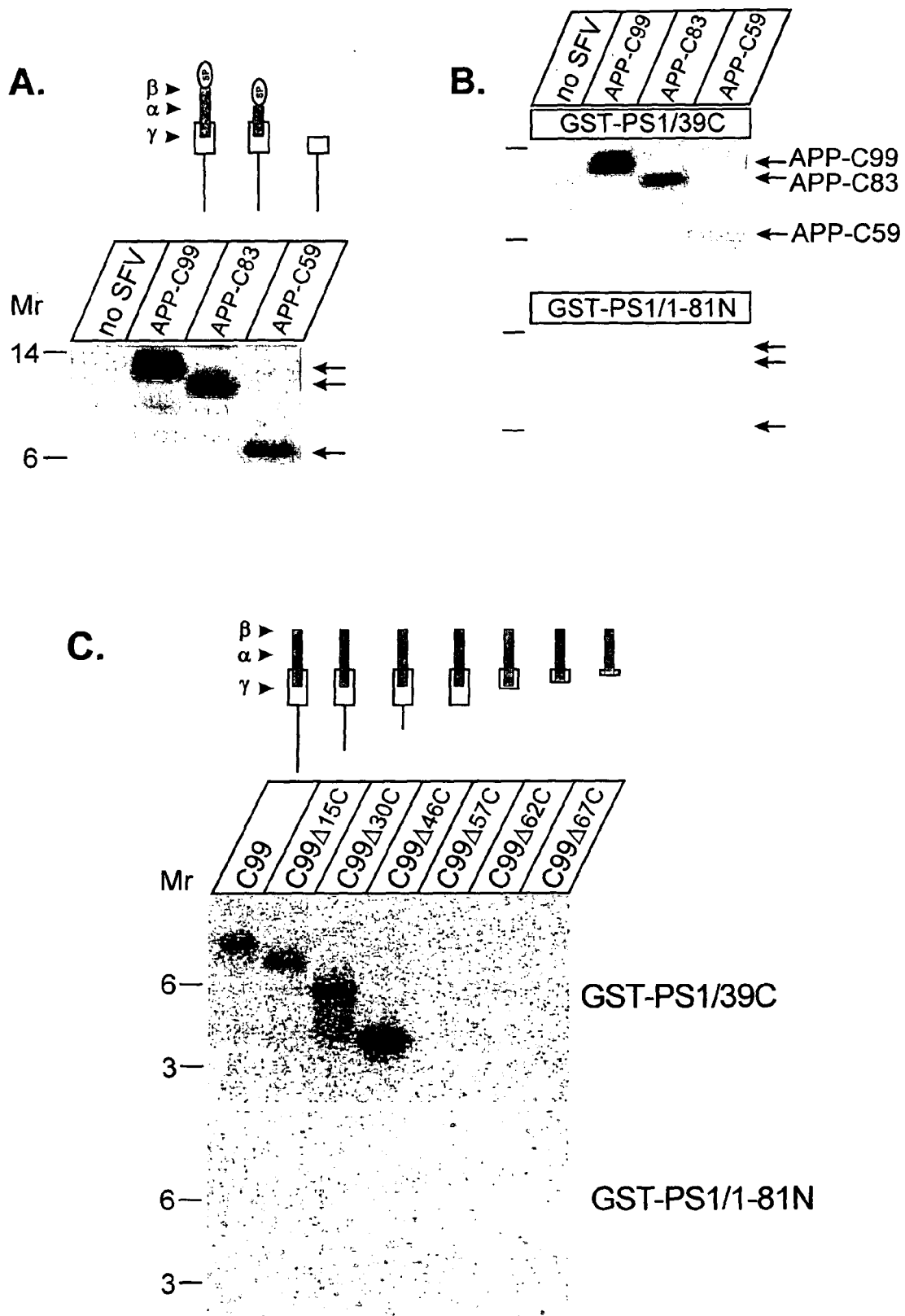

FIG. 3: Mapping the PS1-binding domain in APP.

Part A. Schematic drawing and expression in neurons of the different APP C-terminal fragments used. These fragments represent the C-terminal proteolytic products generated by β-, α-, and γ40 secretase cleavage respectively (APP-C99, -C83 and -C59). As the γ40-cleaved fragment is rapidly degraded in cell culture, three dishes were pooled to obtain sufficient amounts of the recombinant fragment. "SP" indicates a signal peptide.

Part B. Binding of [$^{35}$S]-labeled C-terminal APP-stubs to GST-PS1/39C (top) and GST-PS1/1-81N (bottom, control). All secretase cleaved C-terminal fragments interact with GST-PS1/39C. No binding was observed with GST-PS1/1-81N (or with GST, data not shown).

Part C. The C-terminal truncated fragments of APP-C99 expressed by in vitro transcription/translation are displayed in the top panel. [$^{35}$S]-Labeled translation products were incubated with GST-PS1/39C or -PS1/1-81N (control). Binding to GST-PS1/39C is observed with the first four constructs indicating that the cytoplasmic tail of APP is not required for interaction. Deleting the next eleven amino acids located in the C-terminal end of the transmembrane region of APP completely abolished binding.

Figure 4:
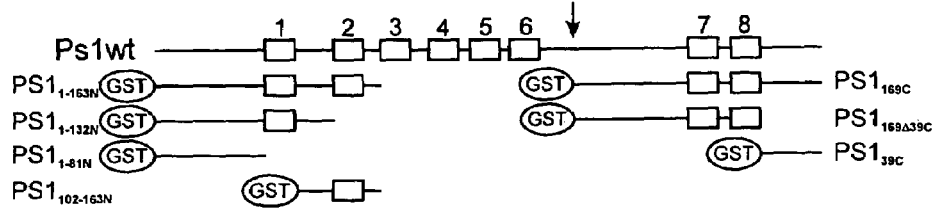
Figure 4:
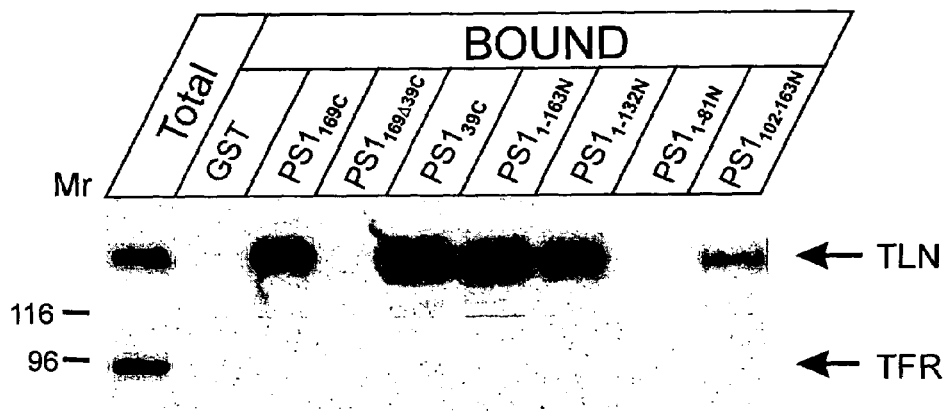
Figure 4:
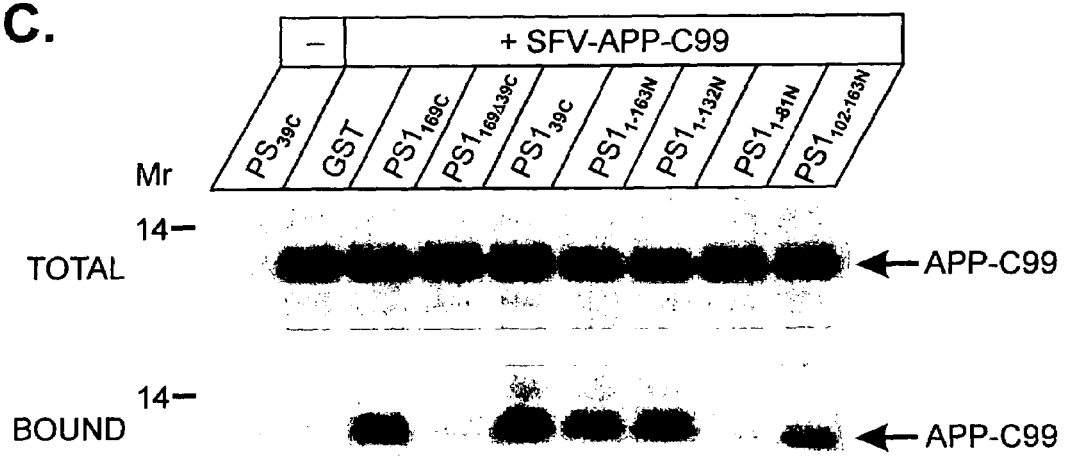

FIG. 4: Delineation of additional binding sites for TLN and APP in PS1.

Part A. Schematic representation of the different GST-PS I fusion proteins that were used. The name of each construct is indicated. Numbers denote the transmembrane regions, arrow points to the cleavage site in PS1.

Part B. Triton-X100 brain extracts were incubated with the fusion proteins and the bound material was analyzed by SDS-PAGE and western blotting using the anti-TLN specific antibody B36.1. Strong binding was observed for all constructs that contained either the first transmembrane region of PS1 or the 39 C-terminal amino acids of PS1. Note that some binding was observed with GST-PS1/102-163N indicating that part of the first intraluminal loop domain may weakly contribute to the binding with TLN. No binding was observed with the transferrin receptor (TFR).

Part C. APP-C99 expressed in primary cortical neurons was labeled using [$^{35}$S]-methionine. Low salt CHAPS-extracts were generated and incubated with the different fusion proteins displayed in FIG. 4, Part A. APP-C99 was equally expressed in all cultures (top panel) and interacted quantitatively with exactly the same PS1 fragments as TLN (bottom panel). Similar results were obtained when Triton-X100 was used.

Figure 5:
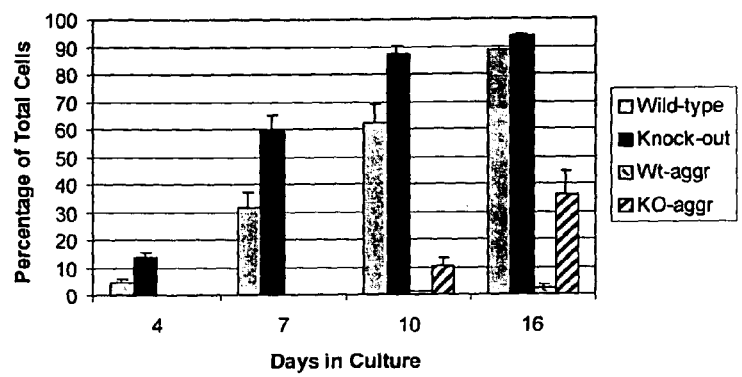
Figure 5:
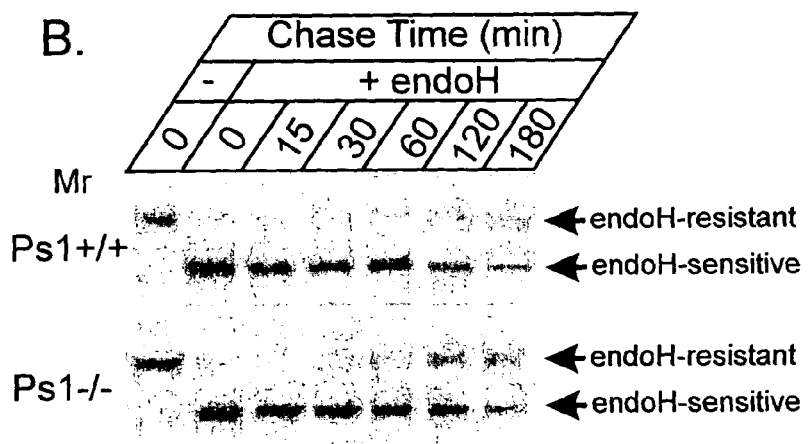
Figure 5:
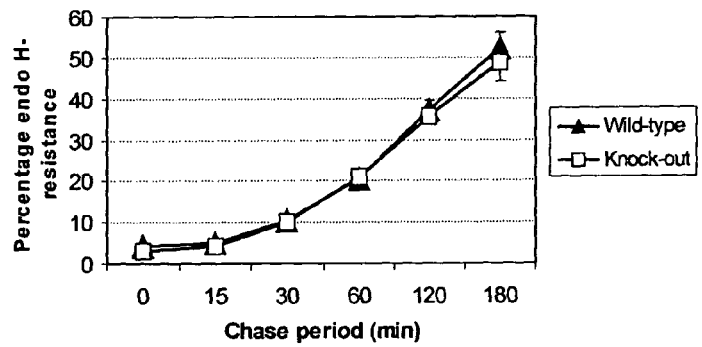
Figure 5:
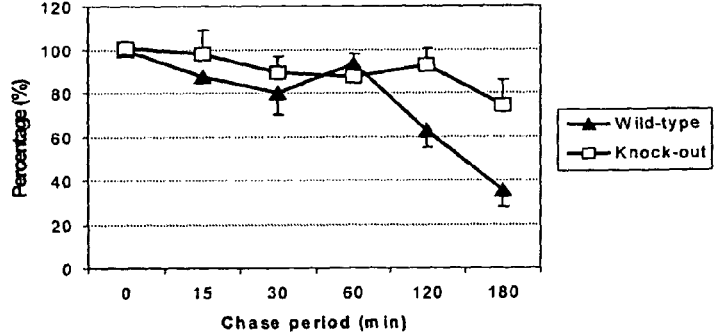

FIG. 5: Developmental regulation and kinetics of TLN expression.

Part A. Time-course of TLN protein expression in developing hippocampal neurons. Neurons from PS1$^{-/-}$ and wild-type littermates were grown for 4, 7, 10 and 16 days, fixed, and immunostained for TLN. The ordinate gives the percentage of neurons at each stage expressing TLN. The number of TLN-positive neurons increases more rapidly in PS1$^{-/-}$ compared to wild-type neurons. At day 10, TLN accumulations in PS1$^{-/-}$ neurons emerged, and at day 16 aggregates were identified in one third of the neurons. Such aggregates were never or very rarely seen in wild-type cultures. Four independent experiments were performed and between 500 and 1200 neurons were counted for each time point (mean±SEM is indicated).

Parts B–D. Turnover but not transport rate of newly synthesized TLN is altered in PS1$^{-/-}$ neurons. Wild type and PS1$^{-/-}$ cortical neurons were transduced with SFV-TLN, pulse-labeled for 15 minutes with [$^{35}$S]-methionine and chased for the time periods indicated. The immunoprecipitated TLN was treated with EndoH and analyzed by phosphorimaging (FIG. 5, Part B). The first lane displays TLN at 0 minute chase without Endo H treatment. Notice the progressive accumulation of an Endo H resistant band, indicating progressive maturation of the sugar chains during traffick through the Golgi apparatus. In FIG. 5, Part C, a quantitative analysis of the experiment displayed in FIG. 5, Part B is shown. No difference was observed between wild type vs. PS1$^{-/-}$ neurons (mean±SEM, n=3).

Part D. The turnover of newly synthesized TLN as deduced from the experiment displayed in FIG. 5, Part B demonstrates that in the absence of PS1 the half-life of SFV-expressed TLN is prolonged (mean±S.E.M., n=3).

Figure 6:
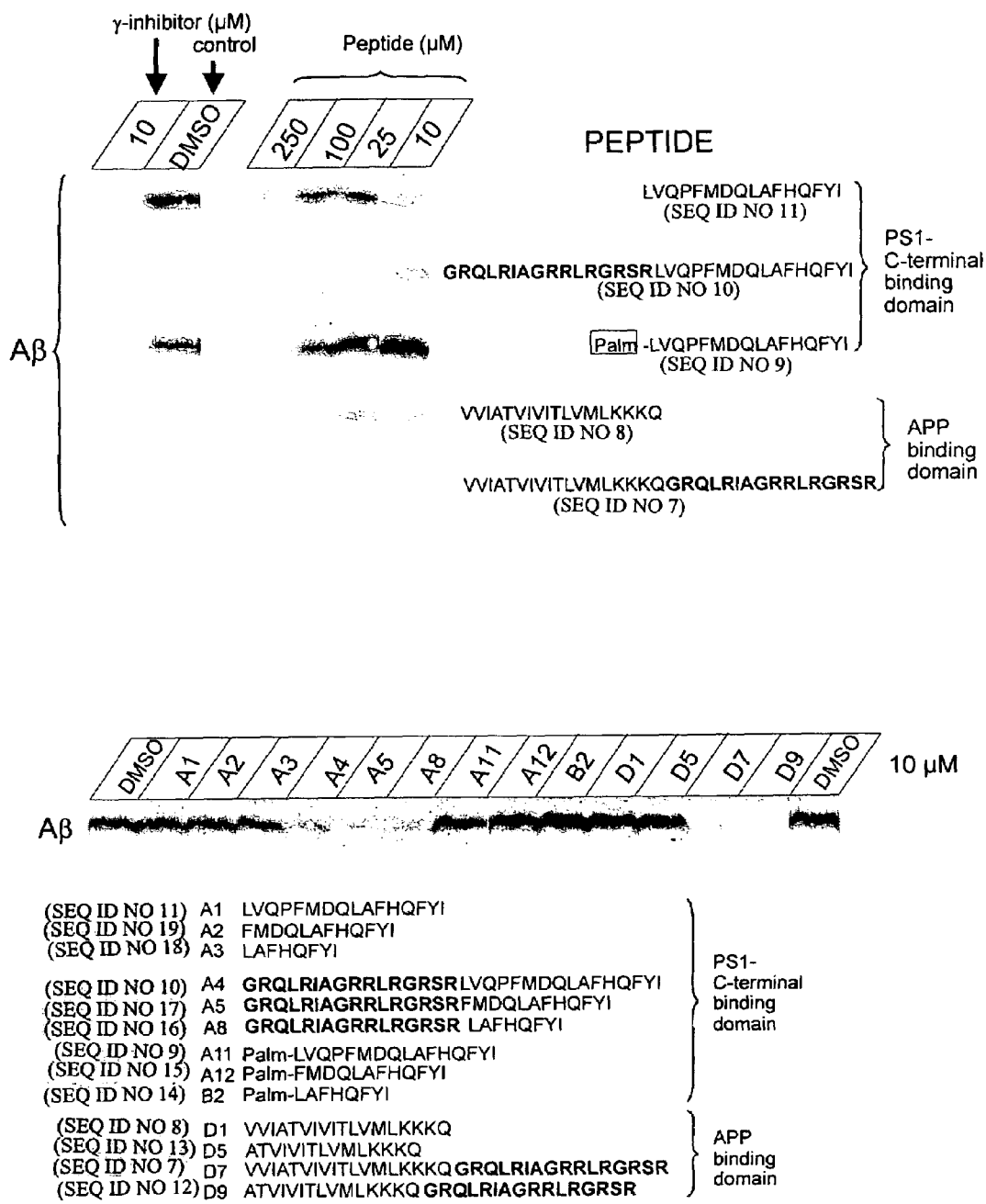

FIG. 6: Peptides that mimic the binding domains in PS1 or APP inhibit the in vitro production of amyloid peptides (Aβ). The PS1-APP binding is mediated by the C-terminus of PS1 (and the first transmembrane domain of PS1) and part of the APP transmembrane region downstream of the γ-secretase cleavage site (and bearing the FAD-associated mutations affecting the γ-secretase cleavage). Peptides mimicking these domains were synthesized as such or with a conserved transmembrane region (TMR) or palmityol group (palm) attached to it. The amino acid sequence of the transmembrane region is NH$_2$-GRQLRIAGRRLRGRSR-COOH (SEQ ID NO:20) and the origin of the TMR is fully described in PCT International Publication WO 02/00882. CHAPS extracts of HeLa cell membranes were incubated with the APP-C99flag-tagged substrate in the presence of DMSO (control) or the different peptides at the concentrations indicated (peptide). γ-secretase inhibitor (10 μM) was included as a positive control for Aβ inhibition. After the reaction, samples were analyzed by SDS-PAGE followed by western blotting using an antibody recognizing Aβ. The binding domains as such only inhibited Aβ production at the highest concentration. However, inhibition was strongly enhanced when the respective peptides were attached to a conserved transmembrane region. The highest inhibition was obtained with peptides comprising the APP binding domain fused to the transmembrane region (the sequence NH$_2$-VVIATVIVITLVMLKKKQ-TMR-COOH (SEQ ID NO:7) and NH$_2$-ATVIVITLVMLK KKQ-TMR-COOH (SEQ ID NO:12).

The invention can be further understood by the following non-limiting examples.

BEST MODE OF THE INVENTION

EXAMPLES

1. TLN Interacts with the Carboxyterminus of PS1

Figure 1:
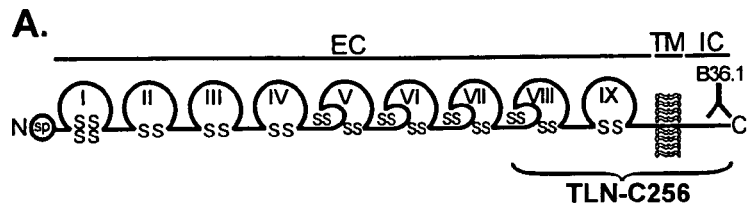
FIG. 1: TLN binds PS1 in vitro.
Figure 1:
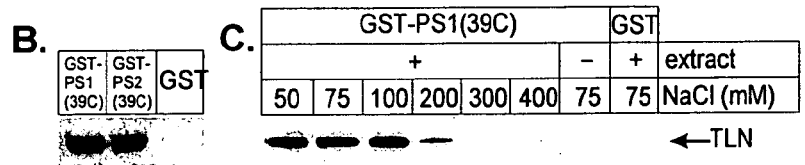
Figure 1:
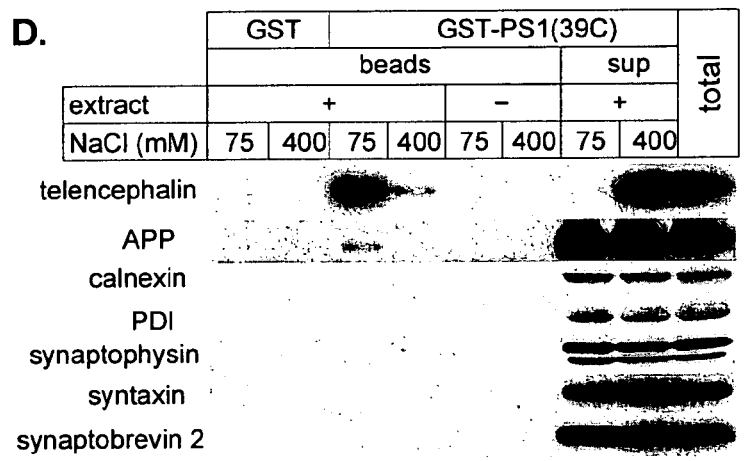
Figure 1:
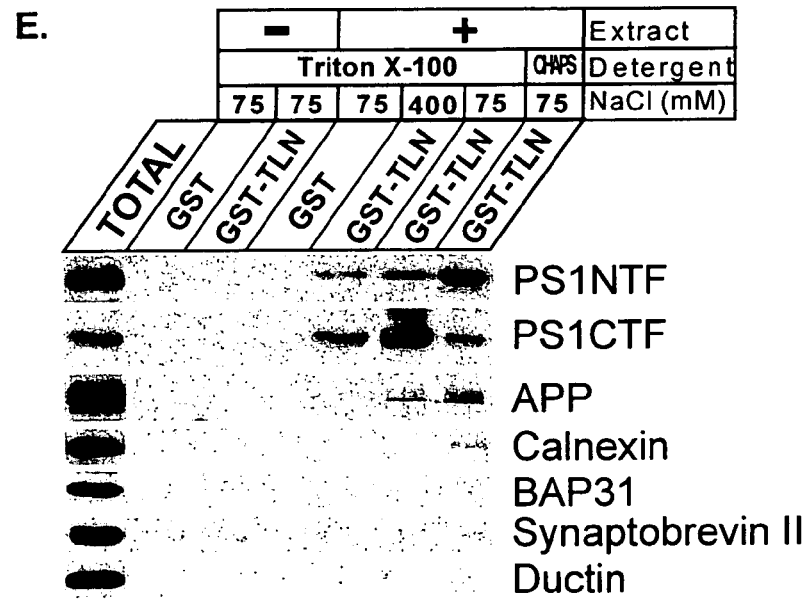

We screened an unamplified mouse hippocampal two-hybrid library with the C-terminal eight amino acids of PS1 (PS1-C8) as bait. A specifically interacting clone containing a cDNA sequence encoding the 256 C-terminal amino acids of TLN (TLN/256C) was obtained. TLN is a neuron specific type I integral membrane glycoprotein belonging to the subfamily of intercellular cell adhesion molecules (ICAM). It contains nine tandem Ig-like domains in the extracellular domain, the two most distal domains being included in TLN/256C (FIG. 1, Part A). Endogenous TLN could be precipitated from Triton X-100 brain extracts using recombinant GST fusion proteins containing the 39 C-terminal residues of PS1 or PS2 (PS1/39C, FIG. 1, Part B). The binding was salt dependent (FIG. 1, Part C). Maximal binding was observed at 75 mM NaCl. (Annaert et al., 1997.) The interaction is specific as demonstrated in FIG. 1, Part D. No, or only weak, binding to GST-PS1/39C was observed with ER-resident proteins like calnexin and PD1, or transmembrane proteins like syntaxin, synaptobrevin II or synaptophysin. We detected a weak signal for endogenous holo-APP only after long exposure (FIG. 1, Part D). The reciprocal experiment using GST-TLN/256C protein confirmed that endogenous PS1-CTF bound to TLN in a salt dependent way (FIG. 1, Part E). Although the PS1-NTF/CTF is Triton-X100 sensitive, minor amounts of PS1-NTF were also detected in precipitates of Triton-X100-extracted membranes. In the presence of 2% CHAPS however, both PS1-NTF and PS1-CTF were recovered on the beads as both fragments remain non-covalently bound under these conditions (Capell et al., 1998). Apparently the binding of the PS complex to GST-TLN/256C in CHAPS is less efficient than the binding of PS1-CTF alone in Triton-X100. Since CHAPS is less denaturing than TX100, it is possible that other proteins of the complex cause steric hindrance under these conditions (Capell et al., 1998). The significance of the weak binding observed with APP is unclear but could reflect the association of APP with PS1 in high molecular weight complexes rather than a direct binding to GST-TLN/256C. Several other controls demonstrate the specificity of the observed binding interaction (FIG. 1, Part E).

2. The First Five Amino Acids of the Transmembrane Domain of TLN are Involved in the Binding to the C-Terminus of PS1.

We generated a series of constructs coding for subdomains of TLN/256C (FIG. 2, Part A) to identify the binding domain. These constructs were expressed using in vitro transcription/translation and assayed for binding to GST-PS1/39C (FIG. 2). Only those constructs that contained the transmembrane region of TLN maintained efficient binding with PS1 (FIG. 2, Part C). However, some caution with this conclusion is indicated because the IC domain of TLN, when expressed alone, tended to form oligomers as can be deduced from its lower mobility in SDS-PAGE (FIG. 2, Part C, Total). This could also explain why this domain did not bind to GST-PS1/39C. Therefore, a series of progressively C-terminal truncated fragments of TLN/256C were generated (FIG. 2, Part D). The first seven fragments (FIG. 2, Part D) maintained binding, while from fragment 8 on almost no binding was observed anymore. Therefore, deletion of the five N-terminal amino acids in the transmembrane domain of TLN/256C accounts for the major loss of binding. It follows that amino acid residues Val$^{829}$-Trp$^{833}$ in the transmembrane region of TLN are essential for binding to GST-PS1/39C.

The eleven last amino acid residues of the transmembrane domain of APP are involved in binding to the C-terminus of PS1.

Others have shown that APP-C99, the β-cleaved APP fragment and direct substrate for γ-secretase, can bind to PS1 (Verdile et al., 2000; Xia et al., 2000). Based on our findings with TLN, we therefore hypothesized that an analogous sequence in the transmembrane domain of APP could be responsible for the interaction with PS1. APP-C99 (β-cleaved stub), APP-C83 (α-cleaved stub) and APP-C59 (the γ40-cleaved cytoplasmic domain of APP) were expressed in wild-type neuron cultures (FIG. 3, Part A) and tested for interaction with GST-PS1/39C. All three C-terminal APP fragments specifically bound to GST-PS1/39C, but not to GST-fused with the N-terminus of PS1 (FIG. 3, Part B). Therefore the PS binding region in APP must be located distally to the γ40 cleavage site in the transmembrane domain of APP. We generated consequently a series of C-terminal truncated APP-C99 constructs, expressed them using in vitro transcription/translation and analyzed their binding to immobilized GST-PS1/39C as above (FIG. 3, Part C). C-terminal truncation up to the transmembrane region of APP did not affect binding to PS1. However, the further removal of eleven amino acids, i.e. up to the γ42 cleavage site in the transmembrane domain of APP, completely abolished binding of APP to PS1/39C. This hydrophobic region (Thr$^{639}$-Lys$^{649}$, based on APP695) is therefore essential for binding to PS1. Importantly, this short amino acid stretch encompasses all known FAD-causing mutations that directly affect γ-secretase cleavage of APP.

3. Delineation of the TLN and APP Binding Domains in PS1.

We noticed in our initial experiments that some PS1-NTF bind to the GST-TLN/256C fusion proteins (FIG. 1, Part E) even in the presence of Triton-X100, i.e. a condition that dissociates the PS1NTF/CTF complex (Capell et al., 1998). This suggests a direct interaction with GST-TLN/256C. To analyze this further different subdomains of PS1 (FIG. 4, Part A) were fused to GST and their ability to bind endogenous TLN from Triton X-100 brain extracts was assessed. Confirming our previous observations, all fusion proteins that contained the C-terminal 39 amino acids of PS1 displayed specific binding to TLN, while deletion of the C-terminus (GST-PS1/169Δ39C) abolished binding. We observed however that GST-PS1/1-163N, i.e. the N-terminal fragment including the first two transmembrane regions, was also binding efficiently to TLN from the brain extracts. Removal of the second transmembrane region did not affect binding, while further removal of the first transmembrane domain (GST-PS1/1-81N), abolished the binding. GST-PS1/102-163N containing the first intraluminal domain and transmembrane domain 2 displayed a rather weak interaction with TLN (FIG. 4, Part B), indicating that it may weakly contribute to the interaction with TLN. Thus besides the carboxyterminal domain, also the first transmembrane domain (Val[82]-Ser[102]) and possibly part of the first loop domain of PS1 can bind TLN. We confirmed that this binding interaction also required the five N-terminal amino acids in the transmembrane domain of TLN (data not shown).

Interestingly, APP-C99 expressed in neuronal cultures bound to exact the same fragments as TLN (FIG. 4, Part C), corroborating the conclusion that APP and TLN bind to very similar sites in PS1.

4. TLN does not Colocalize with PS1 Under Steady State Conditions.

TLN is a glycosylated cell adhesion protein that is exclusively expressed in neurons of the telencephalon (Benson et al., 1998; Yoshihara et al., 1994). We therefore focused on the analysis of endogenous TLN in differentiated hippocampal neurons cultured in vitro. TLN specifically localized to the somatodendritic plasma membrane. The axons, visualized using anti-Tau antibodies remained negative. TLN displayed a typical reticular staining pattern in horizontal sections and a typical focal adhesion pattern when viewed from laterally, in accordance with its role in neurite outgrowth and heterophilic cell-cell interactions (Tamada et al., 1998; Tian et al., 2000; Tian et al., 1997). Surprisingly, little or no colocalization was observed between TLN and PS1, neither in horizontal, nor in vertical sections. Interestingly however, PS1-positive compartments, probably ER (Annaert et al., 1999), tended to closely tether to focal adhesion sites visualized by TLN immunoreactivity.

5. Missorting of TLN in PS1$^{-/-}$ Hippocampal Neurons.

In order to demonstrate the physiological significance of the TLN-PS1 interaction, we next analyzed the effects of PS1 deficiency on TLN expression and localization in neurons. While PS1$^{-/-}$ embryos die late in embryogenesis (Hartmann et al., 1999; Shen et al., 1997; Wong et al., 1997), their hippocampal region at day E17 is sufficiently developed to allow derivatisation of primary cultures of hippocampal neurons. No major differences were observed between wild type and PS1$^{-/-}$ deficient neurons in terms of neuronal polarization and differentiation although this remains to be studied in more detail. However, TLN immunostaining patterns were markedly affected by PS1 deficiency. Particularly in fully polarized neurons, TLN immunoreactivity accumulated in large aggregates. Stereoscopical reconstitution demonstrated that these aggregates were organized in honeycomb structures near to, or at, the cell surface. Vertical sectioning confirmed the localization of the aggregates close to, or at, the cell membrane. The aggregates could be immunostained with antibodies directed to the N-terminus as well as to the C-terminus of TLN indicating that probably full-length TLN accumulated in these structures. These accumulations were not seen in the dendrites. The overall increase in fluorescence intensity indicated finally that more TLN was expressed in the PS1–/– neurons than in wild-type controls.

We next investigated at what subcellular level TLN accumulated in the neurons. The lack of colocalization of TLN aggregates with the nuclear marker Topro-3, the ER marker-BIP, the IC marker ERGIC-53 or the cis-Golgi marker βCOP suggested a post-Golgi localization. We then visualized actin filaments using phalloidin. Only in PS1–/– neurons intense clusters of phalloidin staining were observed in the cell body closely associated with the TLN aggregates. This indicated a local distortion of the actin cytoskeleton probably caused by the accumulating TLN as this was never observed in wild-type neurons. Vertical sections further corroborated the close juxtaposition of actin and TLN. At this resolution it cannot be distinguished whether the TLN immunoreactivity reflects gigantic focal adhesion contacts or a distinct membrane-bound compartment. In any event, TLN accumulation in PS1$^{-/-}$ neurons triggers actin filaments to assemble near these sites.

6. PS1 Regulates the Turnover of TLN

TLN is only detected clearly in brain after birth and rises then rapidly to stable levels within the next month (Yoshihara and Mori, 1994). This increase occurs concomitantly with the intense neurite outgrowth and the establishment of synaptic contacts characteristic of the developing brain. This developmental regulation is equally preserved in the hippocampal neuron cultures. As demonstrated before (Dotti et al., 1988; Goslin and Banker, 1991), hippocampal neurons in culture go progressively through five stages of development. These stages are characterized by the progressive acquisition of a fully polarized phenotype. Stage 5 neurons display full axonal and dendritic compartmentalization and synapse formation. We found that at day 4 post-plating (reflecting early stage 4 (Dotti et al., 1988)) only a fraction of the wild-type neurons expressed TLN. This number increased rapidly resulting in about 90% TLN-positive neurons at day 15. In PS1–/– cultures in contrast, already a significant 15% of the neurons displayed TLN immunoreactivity at day 4, and the maximum frequency was already reached at about 10 days (FIG. 5, Part A). From this stage on, TLN-immunoreactive aggregates were detected (7% of the positive cells). At day 16, TLN aggregates were observed in about one third of the PS1–/– neurons while they remained almost absent in wild-type neurons.

To determine whether the accelerated TLN-expression in PS1$^{-/-}$ neurons is due to an increased transport rate in the secretory pathway, we performed pulse-chase experiments, assessing the rate of glycosylation/maturation using endo H (FIG. 5, Parts B-D). Immediately after pulse labeling, all newly synthesized TLN is endo H sensitive (FIG. 5, Part B). With increasing chase time TLN becomes progressively endo H resistant indicating transport through the Golgi apparatus. Quantitative analysis of this process (FIG. 5C) did not reveal any differences in the acquirement of endo H resistant glycosylation of TLN in wild type versus PS1$^{-/-}$ neurons. In contrast, when we assessed the turnover rate of TLN, a significant difference between wild type and PS1–/– neurons could be demonstrated. The absence of PS1 significantly delayed the degradation of TLN (FIG. 5, Part D).

Since PS1 is involved in the transmembrane proteolysis of APP and Notch, we tested the hypothesis whether TLN is processed by a γ-secretase activity as well. Because proteolytic removal of the ectodomain is believed to be needed before γ-secretase cleavage can occur (Brown et al., 2000; Struhl and Adachi, 2000), and in analogy with the mNotchΔE construct (De Strooper et al., 1999; Schroeter et al., 1998), we generated a TLNΔE construct. Expression of this construct in wild type and PS1 knockout neurons did not reveal any PS1-dependent γ-secretase cleaved fragment.

7. Screening for Compounds in a Cell-Based Assay.

Non-neuronal or neuronal cell lines are transiently or stably transfected with cDNA constructs encoding the carboxytenminal 99 aa of APP fused to its own signal peptide to assure proper orientation in the plane of the membrane (APP-C99). Alternative APP-C99 constructs bearing Familial Alzheimer's Disease (FAD) causing mutations located distal to the γ-secretase cleavage site are considered. Cells expressing either of these recombinant proteins are incubated with cell-permeable peptides or peptido-mimetics, as described herein, designed to compete for the binding sites of PS1 (or PS2) with type I transmembrane proteins (for instance APP and TLN). The first transmembrane domain and the carboxyterminal 8 amino acids of PS1 or PS2 are used as templates to design inhibitory peptides or peptidomimetics.

Non-transfected cells or "scrambled" peptides are used as negative controls. Established γ-secretase inhibitors are used as positive controls.

At the end of the incubation period, conditioned media and cell extracts are analyzed for total Aβ or Aβ40 and Aβ42. Aβ peptides are assayed by ELISA or SDS/PAGE combined with western blotting using peptide specific antibodies. The screening focuses on compounds that inhibit total Aβ secretion/production or selectively Aβ40 or Aβ42.

8. Screening for Compounds in a Cell-Free Assay.

A vector bearing cDNA, encoding APP-C99, including a his-tag or HA-tag, or fused to GST is transformed into *E. coli* and induced to express the tagged recombinant protein. Alternatively, mutations at the γ-secretase cleavage site associated with FAD are introduced. Recombinant tagged APP-C99 is affinity purified on nickle resin, HA-antibody immobilized on protein A or G Sepharose or on glutathione beads respectively. Bound recombinant APP-C99 is eluted, dialyzed, concentrated and aliquoted prior to use in the cell-free assay.

Fixed amounts of recombinant APP-C99 are mixed with cleared cell extracts (for example extracted with Triton X100, CHAPS, CHAPSO or Nonidet p40) and incubated overnight at 37° C. or 4° C. De novo formed Aβ is monitored by SDS/PAGE combined with western blotting. Specific antibodies are used to distinguish Aβ40 from Aβ42 peptides.

The assay is used to test compounds (peptides or peptidomimetics) that are designed to interfere with the binding of PS1 (or PS2) with APP (or TLN). These compounds are mixed with recombinant APP-C99 and cell extracts. The assay can screen for compounds that interfere with Aβ production through interfering with the interaction of PS1 (or PS2) with APP (or TLN). As shown in FIG. 6, several peptides that mimic the binding domains in PS1 or APP inhibit the in vitro production of amyloid peptides. Strong inhibition was obtained with the APP binding domain fused to a transmembrane region (NH$_2$-GRQLRIAGRRLRGRSR-COOH (SEQ ID NO:20), described in PCT International Publication WO 02/00882).

9. Screening for Compounds that Modulate the Turnover of Type I Transmembrane Proteins.

Full-length telencephalin (TLN) or APP are stably transfected in a neuronal cell line (examples are Neuro2A, PC12, NT2N, SH-SY5Y, or wild-type and PS-deficient embryonic stem cells that are allowed to acquire a neuronal phenotype). Culture dishes/plates with semi-confluent cell layers are preincubated with cell-permeable peptides or peptido-mimetics (described under section 1, including negative and positive controls). Next, cells are metabolically ([$^{35}$S]-methionine) pulsed (10 to 30 minutes) and chased for 0 hours or 3 hours in the absence of label. At the end of the experiment cells are lysed and radiolabeled TLN (or APP) is immunoprecipitated using specific polyclonal antibodies. Bound radiolabeled proteins are separated by SDS-PAGE and analyzed using phosphorimaging. The ratio of 3 hours over 0 hours pulse is a measure for the turnover of the radiolabeled protein. The assay screens for compounds that inhibit or delay the turnover of TLN or APP. As positive controls, TLN (or APP) is transduced in neuronally differentiated PS-deficient embryonic stem cells. This assay, in combination with previous assays monitoring Aβ production, enables to distinguish different cell biological functions of PS1 or PS2.

10. Screening for Compounds that Modify the Binding of PS1 (or PS2) to Type I Transmembrane Proteins.

Synthetic peptides comprising the first transmembrane domain or the carboxyterminal 8 aa of PS1 or PS2 (or peptides derived from them) are biotinylated and immobilized on the Fc2 surface of a streptavidin-sensor chip. Biotinylated synthetic "scrambled" peptides are immobilized on the Fc1 surface. The chips are perfused with solubilized recombinant APP-C99 (or derivatives) or with recombinant TLN-256C (the carboxyterminal 256 aa of TLN) in the absence or presence of peptides or peptidomimetics designed to modify the binding of APP-C99 or TLN-256C to the immobilized peptides. Binding is monitored in a BIAcore 2000 instrument (Pharmacia Biosensor) and measured as the difference between Fc2 and Fc1 binding curves. This assay allows high throughput screening of synthetic compounds modifying the interaction of PS1 or PS2 with type I transmembrane proteins.

Materials and Methods

Yeast Two-Hybrid and Vector Construction

Mouse hippocampal mRNA was used to generate a primary lambda library that was converted to a pAD-GAL4 plasmid library by in vivo mass excision (HybriZAP, Stratagene). The sequence coding for the C-terminal eight amino acids of PS1 was cloned into the pBD-GAL4 vector. Yeast was transformed simultaneously with the bait and the library plasmids using the lithium-acetate method (Gietz et al., 1995). His$^+$ colonies were restreaked onto selection agar plates and assayed for lacZ gene expression by the β-galactosidase filter lift assay. We isolated a cDNA sequence encoding the C-terminal 256 amino acids of TLN (TLN/256C) (FIG. 1, Part A).

Production of Recombinant Proteins cDNA's encoding TLN/256C, or various N- and C-terminal fragments of PS1 as indicated were subcloned into pGEX4T-1 (Pharmacia Biotech) and transformed in *E. coli* BL21. GST fusion protein expressed upon induction with 0.1 mM IPTG was released by sonicating the bacteria in Tris-saline buffer (TS, 150 mM NaCl with 10 mM Tris, pH 7.4) containing 100 μg/ml lysozyme, 5 mM DTT, protease inhibitors and 0.5% Sarcosyl (Frangioni and Neel, 1993). Triton X-100 (1% final) was added to the cleared extract and proteins were bound to Glutathione beads (Pharmacia Biotech).

In Vitro Transcription-Translation cDNAs encoding fragments of TLN as indicated in the text were cloned in pcDNAzeo3.1. The APP-C-terminal fragment (APP-C99) was subcloned into pGEM-T. Gradual carboxyterminal truncations of TLN256C and APP-C99 were generated using 5'-sense PCR primer 40 nucleotides upstream of the T7 promoter and 3'-antisense primers corresponding to the respective ends of the truncation. PCR-purified products were directly used in the coupled transcription-translation reaction (TnT system, Promega) in the presence of [$^{35}$S]-methionine. The reaction mixture was diluted 40-fold in low salt buffer (LSB: 75 mM NaCl, 10 mM Tris, 1 mM EDTA, pH 7.4) containing 1% Triton X-100 or 2% CHAPS.

Brain Extracts

Murine cortices were homogenized in 250 mM sucrose containing 10 mM Tris-HCL pH 7.4, 1 mM EDTA (De Strooper et al., 1999). Nuclei and tissue fragments were removed by low speed centrifugation. Microsomal membranes pelleted by high-speed centrifugation (50K rpm, 1 hour) were resuspended in LSB containing 1% Triton X-100 or 2% CHAPS. Aliquots (1 mg/ml) of the cleared extracts (55K rpm, 1 hour) were incubated overnight (4° C.) with immobilized GST fusion proteins. Beads were washed in low salt extraction buffer containing 0.5% Triton X-100 and bound proteins were analyzed by SDS-PAGE and western blotting.

Viral Constructs

The cDNAs encoding the full-length mouse TLN and TLNΔE, which lacks the complete ectodomain, were cloned into the SmaI site of pSFV-1. The pSFV-APPC99 and pSFV-APPC87 vectors encode the signal peptide in continuity with the β-cleaved or α-cleaved C-terminal fragment of APP (Lichtenthaler et al., 1999). pSFV-APPC59 encodes the C-terminal fragment of APP generated by $\gamma_{40}$-secretase cleavage. Production, harvesting and storage of SFV particles was done as described (Annaert et al., 1999; De Strooper et al., 1995; Olkkonen et al., 1993; Tienari et al., 1996).

Neuronal Transduction and Metabolic Labeling

Primary cultures of murine hippocampal or cortical neurons and transduction of the neurons with recombinant SFV was done as described before (Annaert et al., 1999; De Strooper et al., 1998; De Strooper et al., 1995; Goslin and Banker, 1991). Cells were labeled in medium containing 100 μCi/ml [$^{35}$S]-methionine (NEN) for 4 hours at 37° C. Cultures were washed twice with Dulbecco's PBS, harvested in LSB containing 1% Triton X100 or 2% CHAPS and used for binding studies as indicated above. Samples were separated in NuPAGE 4–12% or 12% gels (Invitrogen). Radiolabeled bands were detected by PhosphorImager (Molecular Dynamics Inc.) and quantified using ImageQuantNT 4.1. For pulse-chase experiments, cells were metabolically labeled for 15 minutes, briefly washed and chased for the indicated time periods. Cells were extracted and labeled proteins were immunoprecipitated as detailed before (Annaert et al., 1999; De Strooper et al., 1998). After a final rinse in phosphate buffer (100 mM phosphate, pH 5.7), bound proteins were digested with 10 mU endoglycosidase H (endoH, Boehringer) in the same buffer for 18 hrs at 37° C. After deglycosylation, beads were eluted with sample buffer and analyzed by SDS-PAGE and phosphorimaging.

Indirect Immunofluorescence Microscopy

Hippocampal neurons were fixed and processed for double immunofluorescence microscopy as described (Annaert et al., 1999). Alexa488- and Alexa546-conjugated secondary antibodies (1/1000, Molecular Probes) were used for detection. Topro-3 (1/200, Molecular Probes) was added prior to mounting. Immunostaining was captured through a BioRad MRC1024 confocal microscope and final processing was done with Adobe Photoshop 5.2 software (Adobe, Calif.).

Antibodies

Rabbit polyclonal antibody (pab) B36.1 against mouse TLN (FIG. 1, Part A) was raised against the 18 C-terminal amino acids GAEGGAETPGTAESPADG (SEQ ID NO:21) of mouse TLN coupled to KLH (Pierce). Pab B17.2, B32.1, B19.2 and mab 5.2 against PS1 and B11.7 against the C-terminus of APP have been described (Annaert et al., 1999; De Strooper et al., 1997; De Strooper et al., 1995). Anti-ductin was generated using the peptide antigen MADIKNNPEYSS-KLH (SEQ ID NO:22). Monoclonal antibodies (mab) against synaptobrevin II (clone 69.1), synaptophysin (clone 7.2) and syntaxin I (clone 78.1) were kind gifts of R. Jahn (MPI-Biophysical Chemistry, Göttingen, Del.). Anti-PDI mab was from Stephen Fuller (EMBL, Heidelberg) and anti-TLN mab (TLN-3) from C. Gahmberg (Helsinki, Finland). Pabs against calnexin, BAP31 and ERGIC-53 were provided by A. Helenius (ETH-Zürich, CH), M. Reth (MPI-Immunologie, Freibourg, Del.) and J. Saraste (Univ. Bergen, Norway). Mab directed against the ER-marker Bip or the cis-Golgi coat protein β-COP were purchased from Sigma. Mab 22C11 against APP and anti-Tau-1 were from Boehringer.

REFERENCES

Annaert, W., and De Strooper, B. (1999). Presenilins: molecular switches between proteolysis and signal transduction. Trends Neurosci 22, 439–443.

Annaert, W. G., Becker, B., Kistner, U., Reth, M., and Jahn, R. (1997). Export of cellubrevin from the endoplasmic reticulum is controlled by BAP31. J Cell Biol 139, 1397–410.

Annaert, W. G., Levesque, L., Craessaerts, K., Dierinck, I., Snellings, G., Westaway, D., St. George-Hyslop, P., Cordell, B., Fraser, P., and De Strooper, B. (1999). Presenilin 1 controls gamma-secretase processing of the amyloid precursor protein in pre-golgi compartments of hippocampal neurons. Journal of Cell Biology 147, 277–294.

Arduengo, P. M., Appleberry, O. K., Chuang, P., and S W, L. H. (1998). The presenilin protein family member SPE-4 localizes to an ER/Golgi derived organelle and is required for proper cytoplasmic partitioning during *caenorhabditis elegans* spermatogenesis [In Process Citation]. J Cell Sci 111, 3645–54.

Arii, N., Mizuguchi, M., Mori, K., and Takashima, S. (1999). Development of telencephalin in the human cerebrum. Microsc Res Tech 46, 18–23.

Benson, D. L., Yoshihara, Y., and Mori, K. (1998). Polarized distribution and cell type-specific localization of telencephalin, an intercellular adhesion molecule. J Neurosci Res 52, 43–53.

Berezovska, O., Frosch, M., McLean, P., Knowles, R., Koo, E., Kang, D., Shen, J., Lu, F. M., Lux, S. E., Tonegawa, S., and Hyman, B. T. (1999). The Alzheimer-related gene presenilin 1 facilitates notch 1 in primary mammalian neurons. Brain Res Mol Brain Res 69, 273–80.

Berezovska, O., McLean, P., Knowles, R., Frosh, M., Lu, F. M., Lux, S. E., and Hyman, B. T. (1999). Notch 1 inhibits neurite outgrowth in postmitotic primary neurons. Neuroscience 93, 433–9.

Brown, M. S., Ye, J., Rawson, R. B., and Goldstein, J. L. (2000). Regulated intramembrane proteolysis: a control mechanism conserved from bacteria to humans. Cell 100, 391–8.

Capell, A., Grunberg, J., Pesold, B., Diehlmann, A., Citron, M., Nixon, R., Beyreuther, K., Selkoe, D. J., and Haass, C. (1998). The proteolytic fragments of the Alzheimer's disease-associated presenilin-1 form heterodimers and occur as a 100–150-kDa molecular mass complex. J Biol Chem 273, 3205–11.

Capell, A., Steiner, H., Romig, H., Keck, S., Baader, M., Grim, M. G., Baumeister, R., and Haass, C. (2000). Presenilin-1 differentially facilitates endoproteolysis of the beta-amyloid precursor protein and notch [In Process Citation]. Nat Cell Biol 2, 205–11.

Citron, M., Westaway, D., Xia, W., Carlson, G., Diehl, T., Levesque, G., Johnson-Wood, K., Lee, M., Seubert, P., Davis, A., Kholodenko, D., Motter, R., Sherrington, R., Perry, B., Yao, H., Strome, R., Lieburburg, I., Rommens, J., Kim, S., Schenk, D., Fraser, P., St George Hyslop, P., and Selkoe, D. J. (1997). Mutant presenilins of Alzheimer's disease increase production of 42-residue amyloid beta-protein in both transfected cells and transgenic mice [see comments]. Nat Med 3, 67–72.

Cruts, M., and Van Broeckhoven, C. (1998). Presenilin mutations in Alzheimer's disease. Hum Mutat 11, 183–90.

Culvenor, J. G., Maher, F., Evin, G., Malchiodi-Albedi, F., Cappai, R., Underwood, J. R., Davis, J. B., Karran, E. H., Roberts, G. W., Beyreuther, K., and Masters, C. L. (1997). Alzheimer's disease-associated presenilin 1 in neuronal cells: evidence for localization to the endoplasmic reticulum-Golgi intermediate compartment. J Neurosci Res 49, 719–31.

De Strooper, B., and Annaert, W. (2000). Proteolytic processing and cell biological functions of the amyloid precursor protein [In Process Citation]. J Cell Sci 113, 1857–70.

De Strooper, B., and Annaert, W. (2001). Where Notch and Wnt signaling meet: the Presenilin hub. J Cell Biol 152, F17-F19.

De Strooper, B., Annaert, W., Cupers, P., Saftig, P., Craessaerts, K., Mumm, J. S., Schroeter, E. H., Schrijvers, V., Wolfe, M. S., Ray, W. J., Goate, A., and Kopan, R. (1999). A presenilin-1-dependent gamma-secretase-like protease mediates release of Notch intracellular domain [see comments]. Nature 398, 518–22.

De Strooper, B., Beullens, M., Contreras, B., Levesque, L., Craessaerts, K., Cordell, B., Moechars, D., Bollen, M., Fraser, P., George-Hyslop, P. S., and Van Leuven, F. (1997). Phosphorylation, subcellular localization, and membrane orientation of the Alzheimer's disease-associated presenilins. J Biol Chem 272, 3590–8.

De Strooper, B., Saftig, P., Craessaerts, K., Vanderstichele, H., Guhde, G., Annaert, W., Von Figura, K., and Van Leuven, F. (1998). Deficiency of presenilin-1 inhibits the normal cleavage of amyloid precursor protein [see comments]. Nature 391, 387–90.

De Strooper, B., Simons, M., Multhaup, G., Van Leuven, F., Beyreuther, K., and Dotti, C. G. (1995). Production of intracellular amyloid-containing fragments in hippocampal neurons expressing human amyloid precursor protein and protection against amyloidogenesis by subtle amino acid substitutions in the rodent sequence. Embo J 14, 4932–8.

Doan, A., Thinakaran, G., Borchelt, D. R., Slunt, H. H., Ratovitsky, T., Podlisny, M., Selkoe, D. J., Seeger, M., Gandy, S. E., Price, D. L., and Sisodia, S. S. (1996). Protein topology of presenilin 1. Neuron 17, 1023–30.

Dotti, C. G., Sullivan, C. A., and Banker, G. A. (1988). The establishment of polarity by hippocampal neurons in culture. J Neurosci 8, 1454–68.

Duff, K., Eckman, C., Zehr, C., Yu, X., Prada, C. M., Perez-tur, J., Hutton, M., Buee, L., Harigaya, Y., Yager, D., Morgan, D., Gordon, M. N., Holcomb, L., Refolo, L., Zenk, B., Hardy, J., and Younkin, S. (1996). Increased amyloid-beta42(43) in brains of mice expressing mutant presenilin 1. Nature 383, 710–3.

Esler, W. P., Kimberly, W. T., Ostaszewski, B. L., Diehl, T. S., Moore, C. L., Tsai, J. Y., Rahmati, T., Xia, W., Selkoe, D. J., and Wolfe, M. S. (2000). Transition-state analogue inhibitors of gamma-secretase bind directly to presenilin-1. Nat Cell Biol 2, 428–434.

Frangioni, J. V., and Neel, B. G. (1993). Solubilization and purification of enzymatically active glutathione S-transferase (pGEX) fusion proteins. Anal Biochem 210, 179–87.

Georgakopoulos, A., Marambaud, P., Efthimiopoulos, S., Shioi, J., Cui, W., Li, H. C., Schutte, M., Gordon, R., Holstein, G. R., Martinelli, G., Mehta, P., Friedrich, V. L., and Robakis, N. K. (1999). Presenilin-1 forms complexes with the cadherin/catenin cell-cell adhesion system and is recruited to intercellular and synaptic contacts. Mol Cell 4, 893–902.

Gietz, R. D., Schiestl, R. H., Willems, A. R., and Woods, R. A. (1995). Studies on the transformation of intact yeast cells by the LiAc/SS-DNA/PEG procedure. Yeast 11, 355–60.

Goslin, K., and Banker, G. (1991). Rat hippocampal neurons in low-density culture. In Culturing Nerve Cells, G. Banker and K. Goslin, eds. (Cambridge, Mass.: MIT Press), pp. 251–281.

Guo, Y., Livne-Bar, I., Zhou, L., and Boulianne, G. L. (1999). *Drosophila* presenilin is required for neuronal differentiation and affects notch subcellular localization and signaling. J Neurosci 19, 8435–42.

Haass, C., and De Strooper, B. (1999). The presenilins in Alzheimer's disease—proteolysis holds the key. Science 286, 916–9.

Haass, C., and Selkoe, D. J. (1993). Cellular processing of beta-amyloid precursor protein and the genesis of amyloid beta-peptide. Cell 75, 1039–42.

Hartmann, D., Strooper, B. D., and Saftig, P. (1999). Presenilin-1 deficiency leads to loss of Cajal-Retzius neurons and cortical dysplasia similar to human type 2 lissencephaly. Curr Biol 9, 719–727.

Hayflick, J. S., Kilgannon, P., and Gallatin, W. M. (1998). The intercellular adhesion molecule (ICAM) family of proteins. New members and novel functions. Immunol Res 17, 313–27.

Herreman, A., Serneels, L., Annaert, W., Collen, D., Schoonjans, L., and De Strooper, B. (2000). Total inactivation of gamma-secretase activity in presenilin-deficient embryonic stem cells. Nat Cell Biol 2, 461–462.

Hino, H., Mori, K., Yoshihara, Y., Iseki, E., Akiyama, H., Nishimura, T., Ikeda, K., and Kosaka, K. (1997). Reduction of telencephalin immunoreactivity in the brain of patients with Alzheimer's disease. Brain Res 753, 353–7.

Hubbard, E. J., Wu, G., Kitajewski, J., and Greenwald, 1. (1997). sel-10, a negative regulator of lin-12 activity in *Caenorhabditis elegans*, encodes a member of the CDC4 family of proteins. Genes Dev 11, 3182–93.

Kang, D. E., Soriano, S., Frosch, M. P., Collins, T., Naruse, S., Sisodia, S. S., Leibowitz, G., Levine, F., and Koo, E. H. (1999). Presenilin 1 facilitates the constitutive turnover of beta-catenin: differential activity of Alzheimer's disease-linked PS1 mutants in the beta-catenin-signaling pathway. J Neurosci 19, 4229–37.

Kim, S. H., Lah, J. J., Thinakaran, G., Levey, A., and Sisodia, S. S. (2000). Subcellular localization of presenilins: association with a unique membrane pool in cultured cells. Neurobiol Dis 7, 99–117.

Kirschenbaum, F., Hsu, S. C., Cordell, B., and McCarthy, J. V. (2000). Substitution of a GSK-3beta Phosphorylation Site in Presenilin 1 Separates Presenilin Function from beta-Catenin Signaling. J Biol Chem 420, 2.

Klopfenstein, D. R., Kappeler, F., and Hauri, H. P. (1998). A novel direct interaction of endoplasmic reticulum with microtubules. Embo J 17, 6168–77.

Kopan, R., and Goate, A. (2000). A common enzyme connects notch signaling and Alzheimer's disease. Genes Dev 14, 2799–806.

Kulic, L., Walter, J., Multhaup, G., Teplow, D. B., Baumeister, R., Romig, H., Capell, A., Steiner, H., and Haass, C. (2000). Separation of presenilin function in amyloid beta-peptide generation and endoproteolysis of Notch. Proc Natl Acad Sci USA 97, 5913–8.

Levitan, D., and Greenwald, I. (1995). Facilitation of lin-12-mediated signalling by sel-12, a *Caenorhabditis elegans* S182 Alzheimer's disease gene. Nature 377, 351–4.

Li, X., and Greenwald, I. (1998). Additional evidence for an eight-transmembrane-domain topology for *Caenorhabditis elegans* and human presenilins. Proc Natl Acad Sci USA 95, 7109–14.

Li, X., and Greenwald, I. (1996). Membrane topology of the *C. elegans* SEL-12 presenilin. Neuron 17, 1015–21.

Li, Y. M., Lai, M. T., Xu, M., Huang, Q., DiMuzio-Mower, J., Sardana, M. K., Shi, X. P., Yin, K. C., Shafer, J. A., and Gardell, S. J. (2000). From the Cover: Presenilin 1 is linked with gamma-secretase activity in the detergent solubilized state. Proc Natl Acad Sci USA 97, 6138–6143.

Li, Y. M., Xu, M., Lai, M. T., Huang, Q., Castro, J. L., DiMuzio-Mower, J., Harrison, T., Lellis, C., Nadin, A., Neduvelil, J. G., Register, R. B., Sardana, M. K., Shearman, M. S., Smith, A. L., Shi, X. P., Yin, K. C., Shafer, J. A., and Gardell, S. J. (2000). Photoactivated gamma-secretase inhibitors directed to the active site covalently label presenilin 1. Nature 405, 689–94.

Lichtenthaler, S. F., Wang, R., Grimm, H., Uljon, S. N., Masters, C. L., and Beyreuther, K. (1999). Mechanism of the cleavage specificity of Alzheimer's disease gamma-secretase identified by phenylalanine-scanning mutagenesis of the transmembrane domain of the amyloid precursor protein. Proc Natl Acad Sci USA 96, 3053–3058.

Lukinova, N. I., Roussakova, V. V., and Fortini, M. E. (1999). Genetic characterization of cytological region 77A-D harboring the presenilin gene of *Drosophila melanogaster*. Genetics 153, 1789–97.

Nakamura, K., Manabe, T., Watanabe, M., Mamiya, T., Ichikawa, R., Kiyama, Y., Sanbo, M., Yagi, T., Inoue, Y., Nabeshima, T., Mori, H., and Mishina, M. (2001). Enhancement of hippocampal LTP, reference memory and sensorimotor gating in mutant mice lacking a telencephalon-specific cell adhesion molecule. Eur J Neurosci 13, 179–189.

Naruse, S., Thinakaran, G., Luo, J. J., Kusiak, J. W., Tomita, T., Iwatsubo, T., Qian, X., Ginty, D. D., Price, D. L., Borchelt, D. R., Wong, P. C., and Sisodia, S. S. (1998). Effects of PS1 deficiency on membrane protein trafficking in neurons. Neuron 21, 1213–21.

Nishimura, M., Yu, G., Levesque, G., Zhang, D. M., Ruel, L., Chen, F., Milman, P., Holmes, E., Liang, Y., Kawarai, T., Jo, E., Supala, A., Rogaeva, E., Xu, D. M., Janus, C., Levesque, L., Bi, Q., Duthie, M., Rozmahel, R., Mattila, K., Lannfelt, L., Westaway, D., Mount, H. T., Woodgett, J., St George-Hyslop, P., and et al. (1999). Presenilin mutations associated with Alzheimer disease cause defective intracellular trafficking of beta-catenin, a component of the presenilin protein complex [see comments]. Nat Med 5, 164–9.

Okochi, M., Eimer, S., Bottcher, A., Baumeister, R., Romig, H., Walter, J., Capell, A., Steiner, H., and Haass, C. (2000). A loss of function mutant of the presenilin homologue sel-12 undergoes abberant endoproteolysis in *Caenorhabditis elegans* and increased A-beta-42 generation in human cells. J Biol Chem.

Olkkonen, V. M., Liljestrom, P., Garoff, H., Simons, K., and Dotti, C. G. (1993). Expression of heterologous proteins in cultured rat hippocampal neurons using the Semliki Forest virus vector. J Neurosci Res 35, 445–51.

Polakis, P. (2000). Wnt signaling and cancer. Genes Dev 14, 1837–51.

Pradier, L., Carpentier, N., Delalonde, L., Clavel, N., Bock, M. D., Buee, L., Mercken, L., Tocque, B., and Czech, C. (1999). Mapping the APP/presenilin (PS) binding domains: the hydrophilic N-terminus of PS2 is sufficient for interaction with APP and can displace APP/PS1 interaction. Neurobiol Dis 6, 43–55.

Ray, W. J., Yao, M., Nowotny, P., Mumm, J., Zhang, W., Wu, J. Y., Kopan, R., and Goate, A. M. (1999). Evidence for a physical interaction between presenilin and Notch. Proc Natl Acad Sci USA 96, 3263–8.

Rogaev, E. I., Sherrington, R., Rogaeva, E. A., Levesque, G., Ikeda, M., Liang, Y., Chi, H., Lin, C., Holman, K., Tsuda, T., and et al. (1995). Familial Alzheimer's disease in kindreds with missense mutations in a gene on chromosome 1 related to the Alzheimer's disease type 3 gene. Nature 376, 775–8.

Sakurai, E., Hashikawa, T., Yoshihara, Y., Kaneko, S., Satoh, M., and Mori, K. (1998). Involvement of dendritic adhesion molecule telencephalin in hippocampal long-term potentiation. Neuroreport 9, 881–6.

Saura, C. A., Tomita, T., Davenport, F., Harris, C. L., Iwatsubo, T., and Thinakaran, G. (1999). Evidence that intramolecular associations between presenilin domains are obligatory for endoproteolytic processing. J Biol Chem 274, 13818–23.

Saura, C. A., Tomita, T., Soriano, S., Takahashi, M., Leem, J. Y., Honda, T., Koo, E. H., Iwatsubo, T., and Thinakaran, G. (2000). The nonconserved hydrophilic loop domain of presenilin (PS) is not required for PS endoproteolysis or enhanced abeta 42 production mediated by familial early onset Alzheimer's disease-linked PS variants. J Biol Chem 275, 17136–42.

Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D., and Younkin, S. (1996). Secreted amyloid beta-protein similar to that in the senile plaques of Alzheimer's disease is increased in vivo by the presenilin 1 and 2 and APP mutations linked to familial Alzheimer's disease [see comments]. Nat Med 2, 864–70.

Schroeter, E. H., Kisslinger, J. A., and Kopan, R. (1998). Notch-1 signalling requires ligand-induced proteolytic release of intracellular domain [see comments]. Nature 393, 382–6.

Selkoe, D. J. (1998). The cell biology of beta-amyloid precursor protein and presenilin in Alzheimer's disease [In Process Citation]. Trends Cell Biol 8, 447–53.

Sestan, N., Artavanis-Tsakonas, S., and Rakic, P. (1999). Contact-dependent inhibition of cortical neurite growth mediated by notch signaling [see comments]. Science 286, 741–6.

Shen, J., Bronson, R. T., Chen, D. F., Xia, W., Selkoe, D. J., and Tonegawa, S. (1997). Skeletal and CNS defects in Presenilin-1-deficient mice. Cell 89, 629–39.

Sherrington, R., Rogaev, E. I., Liang, Y., Rogaeva, E. A., Levesque, G., Ikeda, M., Chi, H., Lin, C., Li, G., Holman, K., and et al. (1995). Cloning of a gene bearing missense mutations in early-onset familial Alzheimer's disease [see comments]. Nature 375, 754–60.

Song, W., Nadeau, P., Yuan, M., Yang, X., Shen, J., and Yankner, B. A. (1999). Proteolytic release and nuclear translocation of Notch-1 are induced by presenilin-1 and impaired by pathogenic presenilin-1 mutations. Proc Natl Acad Sci USA 96, 6959–63.

Soriano, S., Kang, D. E., Fu, M., Pestell, R., Chevallier, N., Zheng, H., and Koo, E. H. (2001). Presenilin 1 negatively regulates beta-catenin/T Cell Factor/Lymphoid Enhancer Factor-1 signaling independently of beta-amyloid precursor protein and Notch processing. J Cell Biol 152, 785–794.

Steiner, H., Kostka, M., Romig, H., Basset, G., Pesold, B., Hardy, J., Capell, A., Meyn, L., Grim, M. L., Baumeister, R., Fechteler, K., and Haass, C. (2000). Glycine 384 is required for presenilin-1 function and is conserved in bacterial polytopic aspartyl proteases. Nat Cell Biol 2, 848–851.

Steiner, H., Romig, H., Grim, M. G., Philipp, U., Pesold, B., Citron, M., Baumeister, R., and Haass, C. (1999). The biological and pathological function of the presenilin-1 Deltaexon 9 mutation is independent of its defect to undergo proteolytic processing. J Biol Chem 274, 7615–8.

Steiner, H., Romig, H., Pesold, B., Philipp, U., Baader, M., Citron, M., Loetscher, H., Jacobsen, H., and Haass, C. (1999). Amyloidogenic function of the Alzheimer's disease-associated presenilin 1 in the absence of endoproteolysis. Biochemistry 38, 14600–5.

Struhl, G., and Adachi, A. (2000). Requirements for presenilin-dependent cleavage of notch and other transmembrane proteins [In Process Citation]. Mol Cell 6, 625–36.

Struhl, G., and Greenwald, I. (1999). Presenilin is required for activity and nuclear access of Notch in *Drosophila* [see comments]. Nature 398, 522–5.

Struhl, G., and Greenwald, I. (2001). Presenilin-mediated transmembrane cleavage is required for Notch signal transduction in *Drosophila*. Proc Natl Acad Sci USA 98, 229–234.

Sugino, H., Yoshihara, Y., Copeland, N. G., Gilbert, D. J., Jenkins, N. A., and Mori, K. (1997). Genomic organization and chromosomal localization of the mouse telencephalin gene, a neuronal member of the ICAM family. Genomics 43, 209–15.

Tamada, A., Yoshihara, Y., and Mori, K. (1998). Dendrite-associated cell adhesion molecule, telencephalin, promotes neurite outgrowth in mouse embryo. Neurosci Lett 240, 163–6.

Thinakaran, G., Borchelt, D. R., Lee, M. K., Slunt, H. H., Spitzer, L., Kim, G., Ratovitsky, T., Davenport, F., Nordstedt, C., Seeger, M., Hardy, J., Levey, A. I., Gandy, S. E., Jenkins, N. A., Copeland, N. G., Price, D. L., and Sisodia, S. S. (1996). Endoproteolysis of presenilin 1 and accumulation of processed derivatives in vivo. Neuron 17, 181–90.

Thinakaran, G., Harris, C. L., Ratovitski, T., Davenport, F., Slunt, H. H., Price, D. L., Borchelt, D. R., and Sisodia, S. S. (1997). Evidence that levels of presenilins (PS1 and PS2) are coordinately regulated by competition for limiting cellular factors. J Biol Chem 272, 28415–22.

Tian, L., Kilgannon, P., Yoshihara, Y., Mori, K., Gallatin, W. M., Carpen, O., and Gahmberg, C. G. (2000). Binding of T lymphocytes to hippocampal neurons through ICAM-5 (telencephalin) and characterization of its interaction with the leukocyte integrin CD11a/CD18 [In Process Citation]. Eur J Immunol 30, 810–8.

Tian, L., Nyman, H., Kilgannon, P., Yoshihara, Y., Mori, K., Andersson, L. C., Kaukinen, S., Rauvala, H., Gallatin, W. M., and Gahmberg, C. G. (2000). Intercellular adhesion molecule-5 induces dendritic outgrowth by homophilic adhesion. J Cell Biol 150, 243–52.

Tian, L., Yoshihara, Y., Mizuno, T., Mori, K., and Gahmberg, C. G. (1997). The neuronal glycoprotein telencephalin is a cellular ligand for the CD11a/CD18 leukocyte integrin. J Immunol 158, 928–36.

Tienari, P. J., De Strooper, B., Ikonen, E., Simons, M., Weidemann, A., Czech, C., Hartmann, T., Ida, N., Multhaup, G., Masters, C. L., Van Leuven, F., Beyreuther, K., and Dotti, C. G. (1996). The beta-amyloid domain is essential for axonal sorting of amyloid precursor protein. Embo J 15, 5218–29.

Tomita, T., Takikawa, R., Koyama, A., Morohashi, Y., Takasugi, N., Saido, T. C., Maruyama, K., and Iwatsubo, T. (1999). C terminus of presenilin is required for overproduction of amyloidogenic Abeta42 through stabilization and endoproteolysis of presenilin. J Neurosci 19, 10627–34.

Tomita, T., Tokuhiro, S., Hashimoto, T., Aiba, K., Saido, T. C., Maruyama, K., and Iwatsubo, T. (1998). Molecular dissection of domains in mutant presenilin 2 that mediate overproduction of amyloidogenic forms of amyloid beta peptides. Inability of truncated forms of PS2 with familial Alzheimer's disease mutation to increase secretion of Abeta42. J Biol Chem 273, 21153–60.

Verdile, G., Martins, R. N., Duthie, M., Holmes, E., Hyslop, P. S., and Fraser, P. E. (2000). Inhibiting amyloid precursor protein C-terminal cleavage promotes an Interaction with presenilin 1. J Biol Chem.

Weidemann, A., Paliga, K., Duinwang, U., Czech, C., Evin, G., Masters, C. L., and Beyreuther, K. (1997). Formation of stable complexes between two Alzheimer's disease gene products: presenilin-2 and beta-amyloid precursor protein. Nat Med 3, 328–32.

Wolfe, M. S., Citron, M., Diehl, T. S., Xia, W., Donkor, I. O., and Selkoe, D. J. (1998). A substrate-based difluoro ketone selectively inhibits Alzheimer's gamma-secretase activity. J Med Chem 41, 6–9.

Wolfe, M. S., Xia, W., Moore, C. L., Leatherwood, D. D., Ostaszewski, B., Rahmati, T., Donkor, I. O., and Selkoe, D. J. (1999). Peptidomimetic probes and molecular modeling suggest that Alzheimer's gamma-secretase is an intramembrane-cleaving aspartyl protease [In Process Citation]. Biochemistry 38, 4720–7.

Wolfe, M. S., Xia, W., Ostaszewski, B. L., Diehl, T. S., Kimberly, W. T., and Selkoe, D. J. (1999). Two transmembrane aspartates in presenilin-1 required for presenilin endoproteolysis and gamma-secretase activity [see comments]. Nature 398, 513–7.

Wong, P. C., Zheng, H., Chen, H., Becher, M. W., Sirinathsinghji, D. J., Trumbauer, M. E., Chen, H. Y., Price, D. L., Van der Ploeg, L. H., and Sisodia, S. S. (1997). Presenilin 1 is required for Notch1 and DII1 expression in the paraxial mesoderm. Nature 387, 288–92.

Wu, G., Hubbard, E. J., Kitajewski, J. K., and Greenwald, 1. (1998). Evidence for functional and physical association between *Caenorhabditis elegans* SEL-10, a Cdc4p-related protein, and SEL-12 presenilin. Proc Natl Acad Sci USA 95, 15787–91.

Xia, W., Ray, W. J., Ostaszewski, B. L., Rahmati, T., Kimberly, W. T., Wolfe, M. S., Zhang, J., Goate, A. M., and Selkoe, D. J. (2000). Presenilin complexes with the C-terminal fragments of amyloid precursor protein at the sites of amyloid beta-protein generation. Proc Natl Acad Sci USA 97, 9299–9304.

Xia, W., Zhang, J., Perez, R., Koo, E. H., and Selkoe, D. J. (1997). Interaction between amyloid precursor protein and presenilins in mammalian cells: implications for the pathogenesis of Alzheimer disease. Proc Natl Acad Sci USA 94, 8208–13.

Yoshihara, Y., and Mori, K. (1994). Telencephalin: a neuronal area code molecule? Neurosci Res21, 119–24.

Yoshihara, Y., Oka, S., Nemoto, Y., Watanabe, Y., Nagata, S., Kagamiyama, H., and Mori, K. (1994). An ICAM-related neuronal glycoprotein, telencephalin, with brain segment-specific expression. Neuron 12, 541–53.

Yu, G., Chen, F., Levesque, G., Nishimura, M., Zhang, D. M., Levesque, L., Rogaeva, E., Xu, D., Liang, Y., Duthie, M., St George-Hyslop, P. H., and Fraser, P. E. (1998). The presenilin 1 protein is a component of a high molecular weight intracellular complex that contains beta-catenin. J Biol Chem 273, 16470–5.

Yu, G., Nishimura, M., Arawaka, S., Levitan, D., Zhang, L., Tandon, A., Song, Y. Q., Rogaeva, E., Chen, F., Kawarai, T., Supala, A., Levesque, L., Yu, H., Yang, D. S., Holmes, E., Milman, P., Liang, Y., Zhang, D. M., Xu, D. H., Sato, C., Rogaev, E., Smith, M., Janus, C., Zhang, Y., Aebersold, R., Farrer, L. S., Sorbi, S., Bruni, A., Fraser, P., and St George-Hyslop, P. (2000). Nicastrin modulates presenilin-mediated notch/glp-1 signal transduction and betaAPP processing [see comments]. Nature 407, 48–54.

Zhang, Z., Hartmann, H., Do, V. M., Abramowski, D., Sturchler-Pierrat, C., Staufenbiel, M., Sommer, B., van de Wetering, M., Clevers, H., Saftig, P., De Strooper, B., He, X., and Yankner, B. A. (1998). Destabilization of beta-catenin by mutations in presenilin-1 potentiates neuronal apoptosis. Nature 395, 698–702.

Zhang, Z., Nadeau, P., Song, W., Donoviel, D., Yuan, M., Bernstein, A., and Yankner, B. A. (2000). Presenilins are required for gamma-secretase cleavage of beta-APP and transmembrane cleavage of Notch-1. Nat Cell Biol 2, 463–465.

What is claimed is:

1. A method for producing a composition, said method comprising:
   identifying a compound capable of modulating the interaction between a presenilin and a type I transmembrane protein, said identifying comprising:
      treating said presenilin and type I transmembrane protein with at least one compound; and
      discovering at least one first compound capable of modulating the interaction between said presenilin and type I transmembrane protein; and
   providing said at least one first compound with a pharmaceutically acceptable carrier;
      wherein said at least one compound is selected from the group consisting of SEQ ID NO: 7 and SEQ ID NO: 12.

2. A compound capable of modulating the interaction between a complex of a presenilin and a type I transmembrane protein, said compound consisting of:
   a peptide selected from the group consisting of SEQ ID NO: 7 and SEQ ID NO: 12.

3. A compound capable of modulating the interaction between a complex of a presenilin and a type I transmembrane protein, said compound consisting of:
   a peptide selected from the group consisting of SEQ ID NO: 5 and SEQ ID NO: 13.

4. A composition comprising:
   a pharmaceutically acceptable carrier; and
   a compound, the compound consisting of a peptide selected from the group consisting of SEQ ID NO: 7 and SEQ ID NO: 12.

5. A composition comprising:
   a pharmaceutically acceptable carrier; and
   a compound, said compound consisting of a peptide selected from the group consisting of SEQ ID NO: 5 and SEQ ID NO: 13.

6. An in vitro method of modulating the interaction between complexes of a presenilin and a type I transmembrane protein, said method comprising:
   adding a compound for modulating the interaction between complexes of a presenilin and a type I transmembrane protein, wherein said compound consists of a peptide selected from the group consisting of SEQ ID NO: 5, SEQ ID NO: 7, SEQ ID NO: 12, and SEQ ID NO: 13; and
   modulating the interaction between complexes of a presenilin and a type I transmembrane protein.

7. The compound of claim 2, wherein the peptide consists of SEQ ID NO:7.

8. The compound of claim 2, wherein the peptide consists of SEQ ID NO:12.

9. The compound of claim 3, wherein the peptide consists of SEQ ID NO:5.

10. The compound of claim 3, wherein the peptide consists of SEQ ID NO:13.

* * * * *

SEQUENCE LISTING

```
<160> NUMBER OF SEQ ID NOS: 22

<210> SEQ ID NO 1
<211> LENGTH: 21
<212> TYPE: PRT
<213> ORGANISM: Artificial
<220> FEATURE:
<223> OTHER INFORMATION: Human transmembrane region 1 of presenilin 1

<400> SEQUENCE: 1

Val Ile Met Leu Phe Val Pro Val Thr Leu Cys Met Val Val Val
1               5                   10                  15

Ala Thr Ile Lys Ser
            20

<210> SEQ ID NO 2
<211> LENGTH: 21
<212> TYPE: PRT
<213> ORGANISM: Artificial
<220> FEATURE:
<223> OTHER INFORMATION: Human transmembrane region 1 of presenilin 2

<400> SEQUENCE: 2

Val Ile Met Leu Phe Val Pro Val Thr Leu Cys Met Ile Val Val
1               5                   10                  15

Ala Thr Ile Lys Ser
            20

<210> SEQ ID NO 3
<211> LENGTH: 8
<212> TYPE: PRT
<213> ORGANISM: Artificial
<220> FEATURE:
<223> OTHER INFORMATION: carboxy-terminal of human presenilin 1

<400> SEQUENCE: 3

Leu Ala Phe His Gln Phe Tyr Ile
1               5

<210> SEQ ID NO 4
<211> LENGTH: 8
<212> TYPE: PRT
```

```
<213> ORGANISM: Artificial
<220> FEATURE:
<223> OTHER INFORMATION: carboxy-terminal of human presenilin 2

<400> SEQUENCE: 4

Leu Ala Ser His Gln Leu Tyr Ile
1               5

<210> SEQ ID NO 5
<211> LENGTH: 11
<212> TYPE: PRT
<213> ORGANISM: Artificial
<220> FEATURE:
<223> OTHER INFORMATION: Part of the transmembrane region of human APP

<400> SEQUENCE: 5

Thr Val Ile Val Ile Thr Leu Val Met Leu Lys
1               5                   10

<210> SEQ ID NO 6
<211> LENGTH: 5
<212> TYPE: PRT
<213> ORGANISM: Artificial
<220> FEATURE:
<223> OTHER INFORMATION: Part of the transmembrane region of
                        telencephalin

<400> SEQUENCE: 6

Val Ala Gly Pro Trp
1               5

<210> SEQ ID NO 7
<211> LENGTH: 34
<212> TYPE: PRT
<213> ORGANISM: Artificial
<220> FEATURE:
<223> OTHER INFORMATION: synthesized peptide
<220> FEATURE:
<221> NAME/KEY: SITE
<222> LOCATION: (19)..(34)
<223> OTHER INFORMATION: conserved transmembrane region

<400> SEQUENCE: 7

Val Val Ile Ala Thr Val Ile Val Ile Thr Leu Val Met Leu Lys Lys
1               5                   10                  15

Lys Gln Cys Arg Gln Leu Arg Ile Ala Gly Arg Arg Leu Arg Gly Arg
            20                  25                  30

Ser Arg

<210> SEQ ID NO 8
<211> LENGTH: 18
<212> TYPE: PRT
<213> ORGANISM: Artificial
<220> FEATURE:
<223> OTHER INFORMATION: synthesized peptide

<400> SEQUENCE: 8

Val Val Ile Ala Thr Val Ile Val Ile Thr Leu Val Met Leu Lys Lys
1               5                   10                  15

Lys Gln

<210> SEQ ID NO 9
<211> LENGTH: 17
<212> TYPE: PRT
<213> ORGANISM: Artificial
<220> FEATURE:
```

```
<223> OTHER INFORMATION: synthesized peptide
<220> FEATURE:
<221> NAME/KEY: misc_feature
<222> LOCATION: (1)..(1)
<223> OTHER INFORMATION: X is any amino acid

<400> SEQUENCE: 9

Xaa Leu Val Gln Pro Phe Met Asp Gln Leu Ala Phe His Gln Phe Tyr
 1               5                  10                  15

Ile

<210> SEQ ID NO 10
<211> LENGTH: 32
<212> TYPE: PRT
<213> ORGANISM: Artificial
<220> FEATURE:
<223> OTHER INFORMATION: synthesized peptide
<220> FEATURE:
<221> NAME/KEY: SITE
<222> LOCATION: (1)..(16)
<223> OTHER INFORMATION: conserved transmembrane region

<400> SEQUENCE: 10

Gly Arg Gln Leu Arg Ile Ala Gly Arg Arg Leu Arg Gly Arg Ser Arg
 1               5                  10                  15

Leu Val Gln Pro Phe Met Asp Gln Leu Ala Phe His Gln Phe Tyr Ile
                20                  25                  30

<210> SEQ ID NO 11
<211> LENGTH: 16
<212> TYPE: PRT
<213> ORGANISM: Artificial
<220> FEATURE:
<223> OTHER INFORMATION: synthesized peptide

<400> SEQUENCE: 11

Leu Val Gln Pro Phe Met Asp Gln Leu Ala Phe His Gln Phe Tyr Ile
 1               5                  10                  15

<210> SEQ ID NO 12
<211> LENGTH: 31
<212> TYPE: PRT
<213> ORGANISM: Artificial
<220> FEATURE:
<223> OTHER INFORMATION: synthesized peptide
<220> FEATURE:
<221> NAME/KEY: SITE
<222> LOCATION: (16)..(31)
<223> OTHER INFORMATION: conserved transmembrane region

<400> SEQUENCE: 12

Ala Thr Val Ile Val Ile Thr Leu Val Met Leu Lys Lys Gln Gly
 1               5                  10                  15

Arg Gly Leu Arg Ile Ala Gly Arg Arg Leu Arg Gly Arg Ser Arg
                20                  25                  30

<210> SEQ ID NO 13
<211> LENGTH: 15
<212> TYPE: PRT
<213> ORGANISM: Artificial
<220> FEATURE:
<223> OTHER INFORMATION: synthesized peptide
```

<400> SEQUENCE: 13

Ala Thr Val Ile Val Ile Thr Leu Val Met Leu Lys Lys Lys Gln
1               5                   10                  15

<210> SEQ ID NO 14
<211> LENGTH: 9
<212> TYPE: PRT
<213> ORGANISM: Artificial
<220> FEATURE:
<223> OTHER INFORMATION: synthesized peptide
<220> FEATURE:
<221> NAME/KEY: misc_feature
<222> LOCATION: (1)..(1)
<223> OTHER INFORMATION: X is any amino acid

<400> SEQUENCE: 14

Xaa Leu Ala Phe His Gln Phe Tyr Ile
1               5

<210> SEQ ID NO 15
<211> LENGTH: 13
<212> TYPE: PRT
<213> ORGANISM: Artificial
<220> FEATURE:
<223> OTHER INFORMATION: synthesized peptide
<220> FEATURE:
<221> NAME/KEY: misc_feature
<222> LOCATION: (1)..(1)
<223> OTHER INFORMATION: X is any amino acid

<400> SEQUENCE: 15

Xaa Phe Met Asp Gln Leu Ala Phe His Gln Phe Tyr Ile
1               5                   10

<210> SEQ ID NO 16
<211> LENGTH: 24
<212> TYPE: PRT
<213> ORGANISM: Artificial
<220> FEATURE:
<223> OTHER INFORMATION: synthesized peptide
<220> FEATURE:
<221> NAME/KEY: SITE
<222> LOCATION: (1)..(16)
<223> OTHER INFORMATION: conserved transmembrane region

<400> SEQUENCE: 16

Gly Arg Gln Leu Arg Ile Ala Gly Arg Arg Leu Arg Gly Arg Ser Arg
1               5                   10                  15

Leu Ala Phe His Gln Phe Tyr Ile
            20

<210> SEQ ID NO 17
<211> LENGTH: 28
<212> TYPE: PRT
<213> ORGANISM: Artificial
<220> FEATURE:
<223> OTHER INFORMATION: synthesized peptide
<220> FEATURE:
<221> NAME/KEY: SITE
<222> LOCATION: (1)..(16)
<223> OTHER INFORMATION: conserved transmembrane region

<400> SEQUENCE: 17

Gly Arg Gln Leu Arg Ile Ala Gly Arg Arg Leu Arg Gly Arg Ser Arg
1               5                   10                  15

Phe Met Asp Gln Leu Ala Phe His Gln Phe Tyr Ile

-continued

```
<210> SEQ ID NO 18
<211> LENGTH: 8
<212> TYPE: PRT
<213> ORGANISM: Artificial
<220> FEATURE:
<223> OTHER INFORMATION: synthesized peptide

<400> SEQUENCE: 18

Leu Ala Phe His Gln Phe Tyr Ile
1               5

<210> SEQ ID NO 19
<211> LENGTH: 12
<212> TYPE: PRT
<213> ORGANISM: Artificial
<220> FEATURE:
<223> OTHER INFORMATION: synthesized peptide

<400> SEQUENCE: 19

Phe Met Asp Gln Leu Ala Phe His Gln Phe Tyr Ile
1               5                   10

<210> SEQ ID NO 20
<211> LENGTH: 16
<212> TYPE: PRT
<213> ORGANISM: Artificial
<220> FEATURE:
<223> OTHER INFORMATION: synthesized peptide
<220> FEATURE:
<221> NAME/KEY: SITE
<222> LOCATION: (1)..(16)
<223> OTHER INFORMATION: conserved transmembrane region

<400> SEQUENCE: 20

Gly Arg Gln Leu Arg Ile Ala Gly Arg Arg Leu Arg Gly Arg Ser Arg
1               5                   10                  15

<210> SEQ ID NO 21
<211> LENGTH: 18
<212> TYPE: PRT
<213> ORGANISM: Artificial
<220> FEATURE:
<223> OTHER INFORMATION: synthesized peptide
<220> FEATURE:
<221> NAME/KEY: MISC_FEATURE
<222> LOCATION: (1)..(18)
<223> OTHER INFORMATION: c-terminal amino acids of mouse TLN
                         coupled to KLN

<400> SEQUENCE: 21

Gly Ala Glu Gly Gly Ala Glu Thr Pro Gly Thr Ala Glu Ser Pro Ala
1               5                   10                  15

Asp Gly

<210> SEQ ID NO 22
<211> LENGTH: 15
<212> TYPE: PRT
<213> ORGANISM: Artificial
<220> FEATURE:
<223> OTHER INFORMATION: synthesized peptide

<400> SEQUENCE: 22

Met Ala Asp Ile Lys Asn Asn Pro Glu Tyr Ser Ser Lys Leu His
1               5                   10                  15
```